(12) United States Patent
Kristensen et al.

(10) Patent No.: US 12,427,492 B2
(45) Date of Patent: Sep. 30, 2025

(54) PHOTO BIOREACTOR AND A CASSETTE SYSTEM FOR GERMICIDAL TREATMENT OF LIQUIDS

(71) Applicant: Lyras DK ApS, Aalborg (DK)

(72) Inventors: Mathias Kræmmergaard Kristensen, Aalborg (DK); Rasmus Mortensen, Aalborg (DK)

(73) Assignee: Lyras DK ApS, Aalborg (DK)

( * ) Notice: Subject to any disclaimer, the term of this patent is extended or adjusted under 35 U.S.C. 154(b) by 699 days.

(21) Appl. No.: 17/764,296

(22) PCT Filed: Sep. 21, 2020

(86) PCT No.: PCT/DK2020/050260
§ 371 (c)(1),
(2) Date: Mar. 28, 2022

(87) PCT Pub. No.: WO2021/063462
PCT Pub. Date: Apr. 8, 2021

(65) Prior Publication Data
US 2022/0339597 A1    Oct. 27, 2022

(30) Foreign Application Priority Data
Oct. 1, 2019   (DK) .......................... PA 2019 01151

(51) Int. Cl.
*B01J 19/12* (2006.01)
*A23B 2/53* (2025.01)
*A23B 70/50* (2025.01)

(52) U.S. Cl.
CPC ............... *B01J 19/123* (2013.01); *A23B 2/53* (2025.01); *A23B 70/50* (2025.01); *B01J 2219/00051* (2013.01); *B01J 2219/00162* (2013.01); *B01J 2219/0801* (2013.01); *B01J 2219/12* (2013.01)

(58) Field of Classification Search
CPC ... A23C 3/076; A23L 2/50; A23L 3/28; A61L 2/10; B01J 19/123; B01J 2219/00049; B01J 2219/00051; B01J 2219/00162; B01J 2219/08; B01J 2219/0801; B01J 2219/12
See application file for complete search history.

(56) References Cited

U.S. PATENT DOCUMENTS

| | | |
|---|---|---|
| 5,894,130 A | 4/1999 | Bach |
| 8,525,126 B2 | 9/2013 | Lee et al. |
| 2002/0096648 A1 | 7/2002 | Kaiser et al. |
| 2004/0248076 A1 | 12/2004 | Kaiser et al. |
| 2006/0076506 A1 | 4/2006 | Duthie, Jr. |
| 2009/0145855 A1 | 6/2009 | Day et al. |
| 2013/0026389 A1 | 1/2013 | Lee et al. |
| 2013/0317422 A1 | 11/2013 | Levenson et al. |
| 2014/0001109 A1 | 1/2014 | Lee et al. |
| 2017/0128603 A1 | 5/2017 | Guamis Alegre et al. |
| 2017/0299289 A1* | 10/2017 | Brais ....................... F24F 13/30 |
| 2017/0303555 A1* | 10/2017 | Livne ......................... A23L 3/26 |
| 2019/0059419 A1 | 2/2019 | O'Donnell |
| 2019/0070325 A1* | 3/2019 | Preminger ................ A61L 2/10 |
| 2020/0178573 A1 | 6/2020 | Naito |
| 2020/0230270 A1* | 7/2020 | Taghipour ................ A61L 2/26 |

FOREIGN PATENT DOCUMENTS

| | | |
|---|---|---|
| CA | 2139924 A1 | 11/1994 |
| DE | 852537 C | 10/1952 |
| EP | 3 456 206 A1 | 3/2019 |
| JP | H11 243929 A | 9/1999 |
| KR | 101195588 B1 * | 10/2012 |
| RU | 2 058 096 C1 | 4/1996 |
| RU | 2 322 811 C2 | 4/2008 |
| WO | WO 2009/024155 A1 | 2/2009 |
| WO | WO 2011/126192 A1 | 10/2011 |
| WO | WO 2018/216709 A1 | 11/2018 |
| WO | WO 2019/057257 A1 | 3/2019 |

OTHER PUBLICATIONS

International Search Report dated Dec. 1, 2020 from PCT Priority Application PCT/DK2020/050260 (4 pages).
International Preliminary Report on Patentability dated Apr. 5, 2022 from PCT Priority Application PCT/DK2020/050260 (8 pages).
Written Opinion dated Dec. 1, 2020 from PCT Priority Application PCT/DK2020/050260 (7 pages).
Nor Abdul Karim Shah et al., "Fruit Juice Production Using Ultraviolet Pasteurization: A Review", Beverages, vol. 2, No. 22, Aug. 5, 2016, 20 pages.
B. Jarvis, et al., "Reconsideration of the derivation of Most Probable Numbers, their standard deviations, confidence bounds and rarity values", Journal of Applied Microbiology; vol. 109, 2010, pp. 1660-1667.
Sebastian Schmidt et al., "Process and Laboratory Scale UV Inactivation of Viruses and Bacteria Using an Innovative Coiled Tube Reactor, *Chemical Engineering and Technology*", vol. 30, No. 7, 2007, pp. 945-950.
Office Action (22 pages including English translation) dated Mar. 1, 2024 out of related Chinese Application 202080068366.6
Search Report (dated Dec. 7, 2023) and corresponding Office Action (dated Dec. 12, 2023) out of corresponding Russian Application No. 2022107899 (6 pages total).
Office Action (6 pages) dated Feb. 25, 2020 out of Danish Priority Application PA 2019 01151 (foreign text).

* cited by examiner

*Primary Examiner* — Krishnan S Menon
*Assistant Examiner* — Tak L Chiu
(74) *Attorney, Agent, or Firm* — Crowell & Moring LLP; John C. Freeman

(57) ABSTRACT

A cassette system capable of a germicidal treatment of highly opaque liquids, featuring a filter, which prevents wavelengths above the UV-C spectrum reaching the liquid being treated, one or more spiral-shaped tubes extending from an inlet end to an outlet end creating a fluidic pathway, and one or more light sources illuminating the one or more spiral-shaped tubes, wherein the one or more light sources emit light in a wavelength range between 180-300 nm.

16 Claims, 15 Drawing Sheets

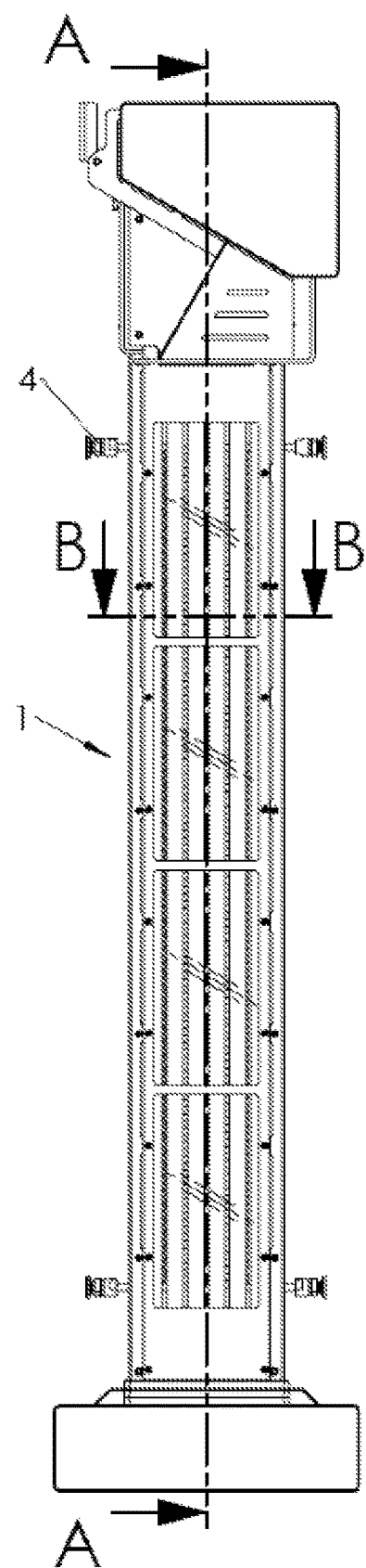
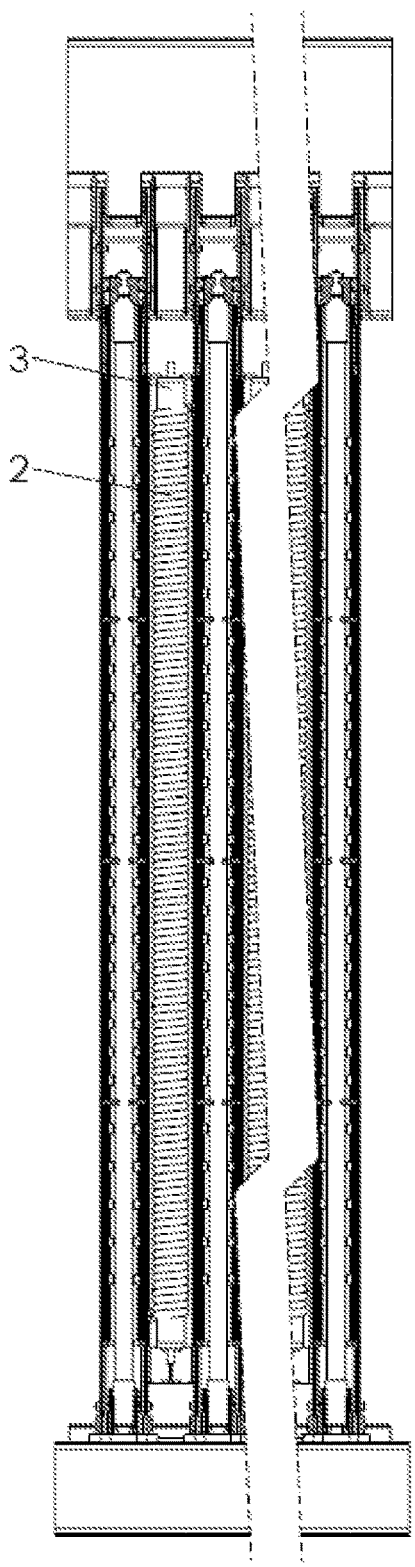
Fig. 2
Fig. 3

SECTION C-C

PHOTO BIOREACTOR AND A CASSETTE SYSTEM FOR GERMICIDAL TREATMENT OF LIQUIDS

This application is a National Stage application of International Application No. PCT/DK2020/050260, filed Sep. 21, 2020, the entire contents of which are incorporated herein by reference.

This application claims priority under 35 U.S.C. § 119 (a) to Danish Patent Application No. PA 201901151, filed on Oct. 1, 2019, the entire contents of each of which are incorporated herein by reference.

BACKGROUND OF THE INVENTION

Field of the Invention

The invention relates to a photo bioreactor and a cassette system, which enables a germicidal treatment of liquids utilizing UV-C light, primarily in the wavelength between 180 nm to 300 nm. The invention relates to a system capable of germicidal treatment of highly opaque liquids.

Description of the Related Art

UV-reactor instruments have previous been used for pasteurization of liquid food products. Examples of such instruments can be found in US Patent Application Publication No. 2002/096648 or Chem. Eng. Technol. 2007, 30, pages 945-950, which both discloses a reactor for irradiating ultraviolet light into a fluid reaction medium. An irradiation chamber is connected to an inlet and an outlet which allows the reaction medium to flow through the reactor while being exposed to ultraviolet light.

Another example of such an UV-reactor instrument is US Patent Application Publication No. 2004/248076, which discloses an apparatus and process for sterilization of liquid media by means of UV irradiation and short-time heat treatment.

However, there is a need within the field for optimizing the killing of bacteria and viruses (i.e. pasteurization or sterilization) while avoiding or lowering the oxidation of the liquid product. Oxidation of the liquid product will result in an enhanced bitter and bad flavor/taste of the food product.

Further, there is a need to simplify such photo bioreactors making it possible to adapt the equipment for an individual task and making it easy to service and clean such system, preferably without the requirement of specialized tools.

SUMMARY OF THE INVENTION

The present invention relates to an UV-reactor instrument for cold pasteurization of liquid food products. Thus, disclosed in a first aspect of the present invention is a photo bioreactor for pasteurization of liquid food products, e.g. milk, the photo bioreactor including a first cassette mounting frame; one or more spiral-shaped tubes extending from an inlet end to an outlet end creating a fluidic pathway; at least two cassettes extending from a first end to a second end; and one or more filters; wherein the cassette mounting frame includes cassette receiving openings into which each of the cassettes are removable mounted, wherein each cassette includes one or more light sources illuminating the one or more spiral-shaped tubes, wherein the one or more light sources emit light in a wavelength range between 180-300 nm, wherein the one or more filters are positioned between the one or more light sources and the one or more spiral-shaped tubes, and wherein the one or more filters prevent light above a wavelength of 300 nm from reaching the one or more spiral-shaped tubes.

By preventing light above a wavelength of 300 nm from reaching the one or more spiral-shaped tubes is meant that light above 300 nm is attenuated by a substantial amount, e.g. at least a factor of 100, or a factor of 1,000 or more.

In one or more embodiments, the one or more filters prevent light above a wavelength of 270 nm from reaching the one or more spiral-shaped tubes.

One of the advantages of using light radiation as a means for cold pasteurization is that it is a very energy efficient way for partial sterilization.

One of the advantages using one or more filters is that photo oxidation from higher wavelengths may be avoided. E.g. avoiding photo oxidation of riboflavin (around a wavelength of 446 nm) is preferred, but also avoiding photo oxidation of other components in the liquid food product, which enhances a bitter and bad flavor/taste in said food product, is preferred. Additionally, the filters may avoid hot air from contacting the one or more spiral-shaped coils, hereby avoiding heating of the liquid food product.

The fluidic pathway is designed to provide a high surface to volume ratio, increasing the exposure of light energy per unit volume with reduced self-shadowing effects from the opaque liquid being treated. In this manner it is possible to treat opaque liquids using light when the material, creating the fluidic pathway, is transparent to the radiation of light.

In a photo bioreactor it is preferred that as large a portion as possible of the UV light reaches the liquid. However, it is also preferable to minimize the visible light and heat radiation and heat transfer via convection to the liquid. By adding a filter, e.g. a band-pass filter, to exclude the unwanted wavelengths and by encapsulating the light sources into a cassette system both the above may be ensured. Further, the cassette system makes it easy to change the light sources during service. As one cassette may be replaced without having to change anything else in the system.

The liquid food product flows through the one or more spiral-shaped tubes with a flow rate. In one or more embodiments, the flow rate measured in millilitres per minutes is between 200-6,000 ml/min, or between 500-4,000 ml/min, or between 800-2,000 ml/min, or between 900-1,100 ml/min.

In one or more embodiments, the one or more light sources are a low pressure germicidal lamp, such as a low-pressure mercury-vapor lamp.

In one or more embodiments, the one or more light sources operate at a lamp temperature between 0° C. and 120° C.

In one or more embodiments, the one or more light sources operate at a lamp temperature between 20° C. and 60° C.

In one or more embodiments, the one or more light sources operate at a lamp temperature between 30° C. and 50° C.

Disclosed herein in a second aspect of the present invention is the use of a photo bioreactor as described throughout this document for cold pasteurization of liquid food products.

Cold pasteurization may be partial sterilization of a substance and especially a liquid in a process where heat is evaded as the main eradication of objectionable organisms without major chemical alteration of the substance. With evaded is not meant excluded but reduced.

In one or more embodiments, a biological contaminant is inactivated or reduced by an order of at least 2-Logo. A biological contaminant may be e.g., bacteria, spores, mold, or virus.

In one or more embodiments, a biological contaminant is inactivated or reduced by an order of at least 3-Logo.

In one or more embodiments, a biological contaminant is inactivated or reduced by an order of at least 4-Logo.

In one or more embodiments, a biological contaminant is inactivated or reduced by an order of at least 5-Logo.

In one or more embodiments, a biological contaminant is inactivated or reduced by an order of at least 6-Logo.

Disclosed herein in a third aspect of the present invention is the use of a photo bioreactor as described throughout this document for killing microorganisms in liquid food products, such as bacteria, mold, spores, or virus.

With killing is meant reducing the amount of active or living microorganisms. Microorganisms found in liquid food products may be present due to contamination during the process of said liquid food product. Common bacteria contamination of e.g. dairy products may be e.g., *Lactobacillus casei, Escherichia coli, Listeria monocytogenes, Salmonella* spp., *Mycobacterium avium* subspecies paratuberculosis (MAP), *Staphylococcus aureus*, or *Streptococcus* spp.

The invention relates to a photo bioreactor including a filter blocking ultraviolet light above 300 nm, and further to a hydraulic design, which enables a germicidal treatment of liquids utilizing UV-C light, ranging from 180 nm to 300 nm.

The invention relates to a system capable of a germicidal treatment of highly opaque liquids. The invention includes a filter, which prevents wavelengths above the UV-C spectrum from reaching the liquid being treated. The cassettes may channel an optional airflow over the one or more light sources. In this manner, the airflow is prevented from reaching a reactor chamber, in which the liquid product is being treated, while maintaining the light sources at their optimal operational temperature. Furthermore, the invention relates to a hydraulic design involving one or more coiled spiral-shaped tubes, which enables crossflows, due to a centrifugal force. This enables most opaque liquids to be treated using UV-C light.

In describing the aspects of the invention specific terminology will be used for the sake of clarity. However, the invention is not intended to be limited to the specific terms so selected, and it is understood that each specific term includes all technical equivalents which operate in a similar manner to accomplish a similar purpose.

Disclosed in a first aspect of the present invention is a photo bioreactor for pasteurization of liquid food products, e.g. milk, the photo bioreactor including a first cassette mounting frame; one or more spiral-shaped tubes extending from an inlet end to an outlet end creating a fluidic pathway; at least two cassettes extending from a first end to a second end; and one or more filters; wherein the cassette mounting frame includes cassette receiving openings into which each of the cassettes are removable mounted, wherein each cassette includes one or more light sources illuminating the one or more spiral-shaped tubes, wherein the one or more light sources emit light in a wavelength range between 180-300 nm, wherein the one or more filters are positioned between the one or more light sources and the one or more spiral-shaped tubes, and wherein the one or more filters prevent light above a wavelength of 300 nm from reaching the one or more spiral-shaped tubes.

Pasteurization is not only limited to partial sterilization of a substance and especially a liquid at a temperature and for a time period of exposure that destroys objectionable organisms without major chemical alteration of the substance, but also covers cold pasteurization which is partial sterilization of a substance and especially a liquid in a process where heat is evaded as the main eradication of objectionable organisms without major chemical alteration of the substance. With evaded is not meant excluded but reduced. The present invention discloses that one of the advantages of using light radiation as a means for cold pasteurization is that it is a very energy efficient way for partial sterilization.

The fluidic pathway is designed to provide a high surface to volume ratio, increasing the exposure of light energy per unit volume with reduced self-shadowing effects from the opaque liquid being treated. In this manner it is possible to treat opaque liquids using light when the material, creating the fluidic pathway is transparent to the radiation of light.

The one or more spiral-shaped tubes extending from an inlet end to an outlet end creating a fluidic pathway utilizes the flow regime occurring when the media is traveling in the fluidic pathway. The flow regime in the fluidic pathway may consists of one or several eddies, which creates a secondary flow axial on the primary flow utilizing the centrifugal force (e.g. Dean vortex flow) to enhance the surface of the liquid being exposed to UV-light emitted by the light sources.

The fluid movement through the fluidic pathway may have a double vortexual pattern consistent with a Dean vortex flow. This provides an axial flow in the fluidic pathway, providing a high surface to volume ratio. This may increase the exposure of light energy per unit volume/surface area with reduced self-shadowing effects from the opaque liquid being treated.

In one or more embodiments, the cassettes are positioned in a parallel configuration.

In one or more embodiments, each cassette also includes one or more of the one or more filters.

In one or more embodiments, one or more of the spiral-shaped tubes are positioned between two of at least two cassettes.

In one or more embodiments, the one or more of the spiral-shaped tubes are grouped in sets of two, such as sets of three, positioned in a configuration alternating between a set of one or more of the spiral-shaped tubes and a cassette.

In one or more embodiments, the photo bioreactor further includes a first ventilation chamber positioned at the first end of the one or more cassettes.

In one or more embodiments, the photo bioreactor further includes a second ventilation chamber positioned at the second end of the one or more cassettes.

In one or more embodiments, the ventilation chamber pulls air out of the cassette or at the ventilation chamber air flows into the cassette.

By drawing air into or out of the cassettes it removes the heat the light source produces. In addition, it is very important to get the most energy and lifespan out of the light sources. This means that they must be cooled evenly and uniformly to their optimum operating temperature. By having ventilation chambers in one or both ends of the cassettes a uniform and optimum operation temperature may be obtained.

In one or more embodiments, the ventilation chamber pulls air out of the cassette at both ends.

The cooling system of the cassettes may work by sucking/pulling air out of both ends. This creates a slightly reduced pressure inside the cassettes.

In one or more embodiments, at the ventilation chamber air flows into the cassette at both ends.

In one or more embodiments, the ventilation chamber pulls air out of the cassette at one end and air flows into the cassette at the other end.

In one or more embodiments, each of the cassettes comprises one or more openings at the first end or the second end for insertion and removal of the one or more light sources.

In one or more embodiments, each of the cassettes further comprises air intake openings for allowing air to flow into the cassette.

In one or more embodiments, each of the cassettes further includes a cassette frame with openings, wherein a first set of openings are covered by glass, e.g. quartz glass, through which light from the light sources can illuminate the one or more of the spiral-shaped tubes.

In one or more embodiments, the glass is kept in position inside the cassette frame by a rubber sealing.

In one or more embodiments, the one or more filters are coated on or incorporated into the glass.

In one or more embodiments, each of the cassettes further includes a cassette frame with openings, wherein a second set of openings are adapted for facilitating internal air movement inside the cassette.

The cassettes further includes small openings in the cassette frames. These openings are designed to be small enough to maintain the negative pressure in the cassette, and they are positioned so that the air that enters cools the lamps uniformly. The openings may e.g. be sized to make the air entering the cassettes flow with a speed of approximately 2 m/s. This means that the air velocity ensures a turbulent stirring of the air in the cassette, which in turn ensures uniform cooling. It further ensures that if the vacuum is uniform within the cassette, air will enter through all the openings. If the openings are too large, air would only enter through the openings closest to where the air is sucked out.

In one or more embodiments, the cassette frame includes two or more frame parts arranged in parallel and wherein the second set of openings are positioned in a non-overlapping manner to ensure that light does not escape from the cassette at positions where the light are not illuminating the one or more spiral-shaped tubes.

The airs path to the openings may be designed so that UV light does not escape through the intake. This ensures that no or very little UV radiation reaches the surroundings, and that the one or more spiral-shaped tubes is not exposed to unfiltered light.

In one or more embodiments, the cassette includes a plurality of openings, wherein an air flow is generated through the plurality of openings when a pressure difference is applied between an internal and external surface of the cassette, and wherein flow of air driven by the pressure difference through the plurality of openings provide a uniform cooling along the entire length of the one or more light sources in order to reach maximum UV output and ensure optimum life time of the one or more light sources.

The plurality of openings in the cassette can be used for cooling of the one or more light sources. The openings can be designed to ensure that if a small pressure difference between the cassette and the surrounding environment is applied it will generate a uniform flow of air through the entire cassette, hereby obtaining an optimal cooling of the one or more light sources. The external and internal surface of the cassette is the outside and inside surface of the cassette, respectively.

In one or more embodiments, the openings are designed so light only escape the cassette towards the one or more spiral-shaped tubes.

In one or more embodiments, a space between the cassette and the one or more spiral-shaped tubes are at least partly lined with polished light reflecting aluminum reflecting light from the one or more light sources, such as reflecting at least 50% of the light back towards the one or more spiral-shaped tubes.

By reflecting light back towards the one or more spiral-shaped tubes is meant that the light hitting the polished light reflecting aluminum if reflected back, hereby preserving parts of the energy in the light, which then is reflected to the one or more spiral-shaped tubes, hereby giving a higher amount of light used to sterilize the liquid in the one or more spiral-shaped tubes. Other materials besides polished aluminum may be used, as long as the material have a high degree of reflection at the desired wavelength.

In one or more embodiments, a space between the cassette and the one or more spiral-shaped tubes are at least partly lined with polished light reflecting aluminum reflecting at least 50% of the light from the one or more light sources back towards the one or more spiral-shaped tubes.

In one or more embodiments, a space between the cassette and the one or more spiral-shaped tubes are at least partly lined with polished light reflecting aluminum reflecting at least 60% of the light from the one or more light sources back towards the one or more spiral-shaped tubes.

In one or more embodiments, a space between the cassette and the one or more spiral-shaped tubes are at least partly lined with polished light reflecting aluminum reflecting at least 70% of the light from the one or more light sources back towards the one or more spiral-shaped tubes.

In one or more embodiments, a space between the cassette and the one or more spiral-shaped tubes are at least partly lined with polished light reflecting aluminum reflecting at least 80% of the light from the one or more light sources back towards the one or more spiral-shaped tubes.

In one or more embodiments, the photo bioreactor further includes a plate limiting or avoiding light from the one or more light sources escaping a space between two cassettes in the photo bioreactor.

By adding a plate to the photo bioreactor to limit or avoiding light in escaping from the space between the cassettes the energy generated from the one or more light sources are preserved within the photo bioreactor herby exposing the liquid within the ore more spiral-shaped tubes to a higher amount of light/energy. Additionally by blocking light in escaping the system potential exposure of hazardous light to a person standing outside the photo bioreactor may be avoided.

If the light cannot escape from the space between the cassettes or from the sides not facing the one or more spiral-shaped tubes, placement of cassettes and spiral-shaped tubes inside a secondary container may be avoided, as the light may potentially be dangerous to humans, and therefore needs to be maintained inside the photo bioreactor. A design where the cassettes and shielding are designed so that light is prevented from escaping is therefore preferable.

In one or more embodiments, a space between two cassettes of the photo bioreactor or a space between a cassette and one or more of the spiral-shaped tubes functions as a ventilation shaft used for cooling of the photo bioreactor, especially cooling the cassettes including the one or more light sources.

There may be a space between the two cassettes in a multiple cassette system or between a cassette and a spiral-shaped tube. Such space may be used to ventilate the air inside the space and preferably exchange the air inside the system with new air, hereby obtaining an air cooling/ventilation of the spiral-shapes tubes and/or the cassettes in the photo bioreactor.

In one or more embodiments, a fluid movement through the one or more spiral-shaped tubes creates a Dean Vortex flow, laminar flow, or turbulent flow.

The present invention discloses that one of the advantages using a Dean Vortex, laminar, or turbulent flow, is that it may increase the exposure of light energy per unit volume/surface area with reduced self-shadowing effects from the opaque liquid being treated, hereby using less energy and time for treatment of the same volume.

Between the one or more spiral-shaped tubes and the one or more light sources may be located one or more filters to narrow the wavelength of the light radiated to the one or more spiral-shaped tubes to a narrower band. This will ensure an optimal wavelength for killing bacteria and viruses while avoiding oxidation of the liquid food product (see FIG. 20).

By preventing light above a wavelength of 300 nm from reaching the one or more spiral-shaped tubes is meant that light above 300 nm is attenuated by a substantial amount, e.g. at least a factor of 100, or a factor of 1000 or more.

In one or more embodiments, the one or more filters prevent light above a wavelength of 290 nm from reaching the one or more spiral-shaped tubes.

In one or more embodiments, the one or more filters prevent light above a wavelength of 280 nm from reaching the one or more spiral-shaped tubes.

In one or more embodiments, the one or more filters prevent light above a wavelength of 270 nm from reaching the one or more spiral-shaped tubes.

In one or more embodiments, the one or more filters prevent light above a wavelength of 260 nm from reaching the one or more spiral-shaped tubes.

In one or more embodiments, a cross-section shape of the one or more spiral-shaped tubes is circular, hexagonal, square, triangular, or oval. The cross-section shape may have any shape, which will still maintain a large exposed outer area of the liquid food product.

In one or more embodiments, the one or more spiral-shaped tubes have an inner tube diameter between 1 mm and 10 mm.

In one or more embodiments, the one or more spiral-shaped tubes have an inner tube diameter between 2 mm and 9 mm.

In one or more embodiments, the one or more spiral-shaped tubes have an inner tube diameter between 3 mm and 8 mm.

In one or more embodiments, the one or more spiral-shaped tubes have an inner tube diameter between 4 mm and 7 mm.

In one or more embodiments, the one or more spiral-shaped tubes have an inner tube diameter between 5 mm and 6 mm.

In one or more embodiments, the one or more spiral-shaped tubes have an inner tube diameter of 5.5 mm.

The size of the inner diameter is a tradeoff between the amounts of liquid food product capable of being treated over a given time versus the exposure of light energy per unit volume/surface area. The larger the inner tube diameter is the more liquid food product can pass over any given time, however, the larger the inner diameter is the smaller (relatively) the exposed area may be.

In one or more embodiments, the one or more spiral-shaped tubes have a pitch between 2 and 8 mm, wherein the pitch is the distance from center to center of the one or more spiral-shaped tubes after one turn/coil of the one or more spiral-shaped tubes.

In one or more embodiments, the one or more spiral-shaped tubes have a pitch between 3 and 7 mm, wherein the pitch is the distance from center to center of the one or more spiral-shaped tubes after one turn/coil of the one or more spiral-shaped tubes.

In one or more embodiments, the one or more spiral-shaped tubes have a pitch between 4 and 7 mm, wherein the pitch is the distance from center to center of the one or more spiral-shaped tubes after one turn/coil of the one or more spiral-shaped tubes.

In one or more embodiments, the one or more spiral-shaped tubes have a pitch of 6 mm, wherein the pitch is the distance from center to center of the one or more spiral-shaped tubes after one turn/coil of the one or more spiral-shaped tubes.

In one or more embodiments, the one or more spiral-shaped tubes have a coil angle between 1° and 6°, such as between 2° and 5°, such as between 3° and 4°, wherein the coil angle is measured between the one or more spiral-shaped tubes and a straight direction compared to the inlet end to the outlet end creating the fluidic pathway.

In one or more embodiments, the one or more spiral-shaped tubes have a coil angle between 2° and 5°.

In one or more embodiments, the one or more spiral-shaped tubes have a coil angle between 3° and 4°.

In one or more embodiments, the one or more spiral-shaped tubes have a coil diameter between 20 and 150 mm, wherein the coil diameter is a distance from outer end to outer end of the one or more spiral-shaped tubes after a half turn/coil of the one or more spiral-shaped tubes. That is, the coil diameter is the width of a coil created by the one or more spiral-shaped tubes.

In one or more embodiments, the one or more spiral-shaped tubes have an outer tube diameter between 2 and 8 mm. In one or more embodiments, the one or more spiral-shaped tubes have an outer tube diameter of between 5 and 6 mm.

In one or more embodiments, the one or more spiral-shaped tubes have an outer tube diameter between 3 and 7 mm.

In one or more embodiments, the one or more spiral-shaped tubes have an outer tube diameter between 4 and 7 mm.

In one or more embodiments, the one or more spiral-shaped tubes have an outer tube diameter of between 5 and 6 mm.

In one or more embodiments, the one or more spiral-shaped tubes have an outer tube diameter of 6 mm.

In one or more embodiments, the one or more spiral-shaped tubes have a wall thickness between 0.1 and 0.4 mm. The wall thickness may also be defined as the outer tube diameter minus the inner tube diameter.

In one or more embodiments, the one or more spiral-shaped tubes have a wall thickness between 0.1 and 0.3 mm.

In one or more embodiments, the one or more spiral-shaped tubes have a wall thickness between 0.2 and 0.3 mm.

In one or more embodiments, the one or more spiral-shaped tubes have a wall thickness between 1 and 4 mm.

In one or more embodiments, the one or more spiral-shaped tubes have a wall thickness between 1 and 3 mm.

In one or more embodiments, the one or more spiral-shaped tubes have a wall thickness between 2 and 3 mm.

A wall thickness between 0.1 and 4 mm is mostly used when the one or more spiral-shaped tubes are made of polymeric material, whereas the wall thickness of 1 to 4 mm is mostly used when quartz glass is used for the one or more spiral-shaped tubes. However, the wall thickness of the one or more tubes depends on the transmission percentage of the light emitted by the one or more light sources. The higher the transmission percentage, the thicker the walls can be made.

In one or more embodiments, the one or more spiral-shaped tubes are coiled around a pillar.

One advantage using a pillar to coil the one or more spiral-shaped tubes around is that a pillar stabilizes the one or more spiral-shaped tubes, if said tubes are e.g. made of a flexible material. The pillar may hence provide stabilization for the coil. Additionally, the pillar may have other advantage, e.g. helping with enhancing the amount of light radiated to the one or more spiral-shaped tubes by being e.g. reflective.

In one or more embodiments, the one or more spiral-shaped tubes are coiled around a pillar so as to create a cone shaped coil. This means that the start of the coil is narrower than the end of the coil, or that the start of the coil is wider than the end of the coil. This may yield a pyramidal shaped coil.

In one or more embodiments, the one or more spiral-shaped tubes include only one spiral-shaped tube around one pillar. In another embodiment, the one or more spiral-shaped tubes are coiled around a pillar in pairs of at least two.

In one or more embodiments, the pillar is made of a reflective material.

Reflective material may be, but is not limited to, dichroic reflector material, such as aluminum, stainless steel, chromium, or silver.

Reflective material may also be partly reflective materials such as Teflon materials, such as perfluoroalkoxy alkanes (PFA), polytetrafluoroethylene (PTFE), fluorinated ethylene propylene (FEP). The reflectiveness of such materials depends on the angle of the light emission on the material.

Polytetrafluoroethylene (PTFE) is a synthetic fluoropolymer of tetrafluoroethylene that has numerous applications. The best known brand name of PTFE-based formulas is Teflon. PTFE is a fluorocarbon solid, as it is a high-molecular-weight compound consisting wholly of carbon and fluorine. PTFE is hydrophobic: neither water nor water-containing substances wet PTFE, as fluorocarbons demonstrate mitigated London dispersion forces due to the high electronegativity of fluorine. PTFE has one of the lowest coefficients of friction of any solid.

Perfluoroalkoxy alkanes (PFA) are fluoropolymers. They are copolymers of tetrafluoroethylene ($C_2F_4$) and perfluoroethers ($C_2F_3OR_f$, where $R_f$ is a perfluorinated group such as e.g. trifluoromethyl ($CF_3$)). The properties of PFA are similar to PTFE. One of the big differences is that the alkoxy substituents allow the polymer to be e.g. melt-processed. On a molecular level, PFA has a smaller chain length, and higher chain entanglement than other fluoropolymers. It also contains an oxygen atom at the branches. This results in a material that is more translucent and has improved flow, creep resistance, and thermal stability close to or exceeding PTFE.

Fluorinated ethylene propylene (FEP) is a copolymer of hexafluoropropylene and tetrafluoroethylene. It differs from the PTFE in that it is melt-processable using conventional injection molding and screw extrusion techniques. Fluorinated ethylene propylene is sold under the brand name Teflon FEP. Other brand names are Neoflon FEP or Dyneon FEP. FEP is very similar in composition to the fluoropolymers PTFE and PFA. FEP is softer than PTFE and melts around 260° C. FEP is highly transparent and resistant to sunlight.

FEP and PFA both share PTFE's useful properties of low friction and non-reactivity, but are more easily formable.

In one or more embodiments, the pillar is made of a reflective polymeric material.

In one or more embodiments, the pillar is covered with a metallized film.

Metalized films are polymer films coated with a thin layer of metal, such as, but not limited to, aluminum. They offer the glossy metallic appearance of an aluminum foil at a reduced weight and cost.

In one or more embodiments, the pillar is made of polytetrafluoroethylene (PTFE).

In one or more embodiments, the one or more spiral-shaped tubes have a compressed length from the inlet end to the outlet end between 100 mm and 400 mm. The compressed length is the length of the one or more spiral-shaped tubes as shaped in the photo bioreactor without pulling or pressing on the one or more spiral-shaped tubes, so as to get a measure from the inlet to the outlet end.

In one or more embodiments, the one or more spiral-shaped tubes have an extension/free length from the inlet end to the outlet end between 5 m and 20 m. The extension/free length is the total length of one tube in the one or more spiral-shaped tubes. The total length of one tube is equal to the total distances one liquid food product unit has to pass through the one or more spiral-shaped tubes.

In one or more embodiments, the one or more spiral-shaped tubes are made of a polymeric or quartz glass material being ultraviolet light transparent. However, the one or more spiral-shaped tubes can be made of any material as long as said material is more or less transparent to the light emitted by the one or more light sources.

In one or more embodiments, the one or more spiral-shaped tubes are selected from fluorinated ethylene propylene (FEP), polytetrafluoroethylene (PTFE), or perfluoroalkoxy alkanes (PFA). The one or more spiral-shaped tubes may be made of any materiel with similar properties of FEP, PTFE, or PFA.

In one or more embodiments, the one or more spiral-shaped tubes are from amorphous fluoropolymer (AF). The one or more spiral-shaped tubes may be made of any materiel with similar properties of AF.

Amorphous fluoropolymer (AF) is a family of amorphous fluoroplastics. These materials are similar to other amorphous polymers in optical clarity and mechanical properties, including strength. These materials are comparable to other fluoroplastics in their performance over a wide range of temperatures, in having excellent chemical resistance, and in having outstanding electrical properties. AF polymers are distinct from other fluoroplastics in that they are soluble in selected solvents, have high gas permeability, high compressibility, high creep resistance, and low thermal conductivity. AF polymers have the lowest dielectric constant of any known solid polymer. AF polymers have a low index of refraction when compared to many other known polymer.

In one or more embodiments, the inlet end and the outlet end is designed such that the liquid food product enters and exits the one or more spiral-shaped tubes axially. This means that liquid will exit from the outlet end more or less axially to where it entered in the inlet end.

In one or more embodiments, the inlet end and the outlet end is designed such that the liquid food product flows overall vertically through the one or more spiral-shaped tubes when observing from inlet end to outlet end. This means that the liquid food product will enter the one or more spiral-shaped tubes through the inlet vertically, flow through the one or more spiral-shaped tubes, and exit the outlet vertically, hereby giving an overall vertical flow.

In one or more embodiments, the inlet end and the outlet end is designed such that the liquid food product flows overall horizontally through the one or more spiral-shaped tubes when observing from inlet to outlet. This means that the liquid food product will enter the one or more spiral-shaped tubes through the inlet horizontally, flow through the one or more spiral-shaped tubes, and exit the outlet horizontally, hereby giving an overall horizontal flow.

In one or more embodiments, the one or more light sources are coupled to one or more fibers guiding the 180-300 nm light from the one or more light sources to the one or more spiral-shaped tubes. This means that the light emitted from the light source is guided via/through one or more fibers to the one or more spiral-shaped tubes. A fiber may be an optical fiber. An optical fiber is a flexible, transparent fiber made by e.g., drawing glass (silica) or plastic to a chosen diameter. Optical fibers may be used as a means to transmit light between the two ends of the fiber.

In one or more embodiments, one light source and multiple fibers are used for illuminating the one or more spiral-shaped tubes.

In one or more embodiments, the one or more light sources are selected from a mercury-vapor lamp, xenon lamp, or a light emitting diode (LED). The light source of the present invention may be any light source suitable for creating light emission in the spectral wavelength area of 180 nm to 300 nm.

A mercury-vapor lamp is a gas discharge lamp that uses an electric arc through vaporized mercury to produce light. The arc discharge may be confined to a small fused quartz arc tube.

A light emitting diode (LED) is a two-lead semiconductor light source. It is a p-n junction diode that emits light when activated. When a suitable voltage is applied to the leads, electrons are able to recombine with electron holes within the device, releasing energy in the form of photons. This effect is called electroluminescence, and the color of the light (corresponding to the energy of the photon) is determined by the energy band gap of the semiconductor. LEDs are typically small (less than 1 mm) and integrated optical components may be used to shape the radiation pattern.

A xenon arc lamp is a specialized type of gas discharge lamp, an electric light that produces light by passing electricity through ionized xenon gas at high pressure. It produces a bright white light that closely mimics natural sunlight. A special kind of xenon lamp is used in automobiles. These are actually metal-halide lamps, where a xenon arc is only used during start-up.

In one or more embodiments, the one or more light sources are a metal-halide lamp. A metal-halide lamp is an electrical lamp that produces light by an electric arc through a gaseous mixture of vaporized mercury and metal halides. It is a type of high-intensity gas discharge lamp. They are similar to mercury-vapor lamps, but contain additional metal halide compounds in the quartz arc tube, which may improve the efficiency and color rendition of the light.

In one or more embodiments, the one or more light sources are selected from a light source emitting light in the ultraviolet C (UV-C) spectral wavelength area.

The ultraviolet spectra may be broken down into several smaller areas, these are: ultraviolet A (UV-A), 315-400 nm; ultraviolet B (UV-B), 280-315 nm; ultraviolet C (UV-C), 100-280 nm; near ultraviolet (N-UV), 300-400 nm; middle ultraviolet (M-UV), 200-300 nm; far ultraviolet (F-UV), 122-200 nm.

In one or more embodiments, the one or more light sources are selected from a light source emitting light in the middle ultraviolet (M-UV) spectral wavelength area.

In one or more embodiments, the one or more light sources are a low pressure germicidal lamp, such as a low-pressure mercury-vapor lamp.

A low pressure germicidal lamp may be a UV lamp that emits a significant portion of its radiative power in the UV-C band, such as a low-pressure mercury-vapor lamp or a low pressure amalgam lamp.

A low pressure amalgam lamp is a lamp doped with mercury combined with another element (often gallium) and hence is also called an amalgam lamp.

In one or more embodiments, the one or more light sources operate at a lamp temperature between 0° C. and 120° C.

In one or more embodiments, the one or more light sources operate at a lamp temperature between 20° C. and 60° C.

In one or more embodiments, the one or more light sources operate at a lamp temperature between 30° C. and 50° C.

The present invention discloses that one of the advantages by utilizing a light source with a lower lamp temperature may be that less heat is transferred from the light source to the liquid food product. This may yield a lower requirement for cooling of the liquid food product during operation of the bioreactor.

In one or more embodiments, the one or more light sources operate at a lamp temperature of 40° C.

The positioning of the cassettes comprising the one or more light sources can be varied according to the overall setup of the bioreactor to achieve the highest possible transfer of energy from the one or more light sources to the liquid food product inside the one or more spiral-shaped tubes.

In one or more embodiments, the one or more filters are selected from band-pass filters, notch filters, or a combination of both.

One of the advantages using one or more filter (e.g. a band-pass filter or a notch filter) may be that photo oxidation from higher wavelengths may be avoided. E.g. avoiding photo oxidation of riboflavin (around a wavelength of 446 nm) is preferred, but also avoiding photo oxidation of other components in the liquid food product, which enhances a bitter and bad flavor/taste in the food product, is preferred. Additionally, the filters may avoid hot air from contacting the one or more spiral-shaped coils, hereby avoiding heating of the liquid food product.

A band-pass filter is a device that passes frequencies within a certain range and rejects/attenuates frequencies outside that range.

A notch filter is a band-stop filter with a narrow stopband. In signal processing, a band-stop filter or band-rejection filter is a filter that passes most frequencies unaltered, but rejects/attenuates those in a specific range to very low levels. It is the opposite of a band-pass filter.

In one or more embodiments, the photo bioreactor further comprises a reactor housing. The reactor housing is modularly designed, and hence does not have a minimum or maximum length. The size of the reactor housing depends on the size of the cassettes, the one or more spiral-shaped tubes, and other features added to the bioreactor. A reactor housing may be desirable as it will contain the light inside the reactor and reflect the light back towards the one or more spiral-shaped tubes.

In one or more embodiments, the one or more spiral-shaped tubes, the cassettes, and the one or more filters are enclosed inside the reactor housing.

In one or more embodiments, the reactor housing is made of a UV-C reflective material. A UV-C reflective material may be a material, which reflects light emitted in the spectral area of 100 nm to 300 nm. By utilizing a reflective UV-C material one advantage may be minimization of the energy needed for reactor to run, as more of the light may be reflected back towards the one or more spiral-shaped tubes.

In one or more embodiments, the reactor housing is made of reflective polytetrafluoroethylene (PTFE).

Polytetrafluoroethylene (PTFE) is a synthetic fluoropolymer of tetrafluoroethylene that has numerous applications. The best known brand name of PTFE-based formulas is Teflon. PTFE is a fluorocarbon solid, as it is a high-molecular-weight compound consisting wholly of carbon and fluorine. PTFE is hydrophobic: neither water nor water-containing substances wet PTFE, as fluorocarbons demonstrate mitigated London dispersion forces due to the high electronegativity of fluorine. PTFE has one of the lowest coefficients of friction of any solid.

In one or more embodiments, the photo bioreactor further includes additional means for air cooling of the one or more light sources or the one or more spiral-shaped tubes. Depending on the lamp temperature additional cooling may be needed to keep the liquid food product at an acceptable temperature while traveling through the fluidic pathway.

In one or more embodiments, the photo bioreactor further includes a control unit.

A control unit may be a unit capable of measuring and controlling e.g., flow speed, temperature, light intensity and various other properties. One of the advantages using a control unit may be an automatic control of the bioreactor. Additionally, with a control unit, a surveillance system may be setup, so that if e.g. the pressure is decreasing, the temperature is increasing, or the light intensity is decreasing, the operator may be notified.

In one or more embodiments, the control unit includes electronic temperature control and flow control.

In one or more embodiments, the control unit automatically controls the lamp temperature and a flow speed of a liquid through the fluidic pathway. Utilizing automatic control may have one of the advantages of the user saving time due to less time spend observing the system and doing manual controlled adjustments of the properties of the system. Additionally, with a control unit, a surveillance system may be setup, so that if e.g. the pressure is decreasing, the temperature is increasing, or the light intensity is decreasing, the operator may be notified. Additionally, the control unit may automatically counter the decrease in pressure, the increase in temperature, or the decrease in light intensity. Alternatively, the control unit may shut down the reactor if not able to counter the different irregularities.

Another aspect of the present invention is the use of a photo bioreactor as described throughout this document for cold pasteurization of liquid food products.

Cold pasteurization may be partial sterilization of a substance and especially a liquid in a process where heat is evaded as the main eradication of objectionable organisms without major chemical alteration of the substance. With evaded is not meant excluded but reduced. The present invention discloses that one of the advantages of using light radiation as a means for cold pasteurization is that it is a very energy efficient way for partial sterilization.

In one or more embodiments, the liquid food products are selected from liquid dairy products.

In one or more embodiments, the liquid food products are selected from raw milk, milk, juice, coffee, tea, soya, soylent, soda, broth, soup, beer, smoothies, protein shake, liquid meal-replacement, cream, wine, mayonnaise, ketchup, syrup, honey, or opaque processing water.

In one or more embodiments, a biological contaminant is inactivated or reduced by an order of at least 2-Logo. A biological contaminant may be e.g., bacteria, spores, mold, or virus.

In one or more embodiments, a biological contaminant is inactivated or reduced by an order of at least 3-Logo.

In one or more embodiments, a biological contaminant is inactivated or reduced by an order of at least 4-Logo.

In one or more embodiments, a biological contaminant is inactivated or reduced by an order of at least 5-Logo.

In one or more embodiments, a biological contaminant is inactivated or reduced by an order of at least 6-Logo.

In one or more embodiments, the biological contaminant is selected from *Campylobacter jejuni, Shigella, Coxiella burnetii, Escherichia coli, Listeria monocytogenes, Mycobacterium bovis, Mycobacterium tuberculosis, Mycobacterium paratuberculosis, Salmonella* spp., *Yersinia enterocolitica, Brucella* spp., *Staphylococcus* spp., *Lactobacillus casei, Mycobacterium avium* subspecies, *Staphylococcus aureus, Streptococcus* spp., *Enterococcus* spp., or *Entrerobacter* spp.

Another aspect of the present invention is the use of a photo bioreactor as described throughout this document for killing microorganisms in liquid food products, such as bacteria, mold, spores, or virus.

With killing is meant reducing the amount of active or living microorganisms. Microorganisms found in liquid food products may be present due to contamination during the process of said liquid food product. Common bacteria contamination of e.g. dairy products may be e.g., *Lactobacillus casei, Escherichia coli, Listeria monocytogenes, Salmonella* spp., *Mycobacterium avium* subspecies paratuberculosis (MAP), *Staphylococcus aureus*, or *Streptococcus* spp.

In one or more embodiments, the liquid food products are selected from liquid dairy products.

In one or more embodiments, the liquid food products are selected from raw milk, milk, juice, coffee, tea, soya, soylent, soda, broth, soup, beer, smoothies, protein shake, liquid meal-replacement, cream, wine, mayonnaise, ketchup, syrup, honey, or opaque processing water.

In one or more embodiments, a biological contaminant is inactivated or reduced by an order of at least 2-Logo, such as at least 3-Logo, such as at least 4-Logo, such as at least 5-Logo, such as at least 6-Logo. A biological contaminant may be e.g., bacteria, spores, mold, or virus In one or more embodiments, a biological contaminant is inactivated or reduced by an order of at least 5-Logo.

In one or more embodiments, a biological contaminant is inactivated or reduced by an order of at least 6-Logo.

In one or more embodiments, the biological contaminant is selected from *Campylobacter jejuni, Shigella, Coxiella burnetii, Escherichia coli, Listeria monocytogenes, Mycobacterium bovis, Mycobacterium tuberculosis, Mycobacterium paratuberculosis, Salmonella* spp., *Yersinia enterocolitica, Brucella* spp., *Staphylococcus* spp., *Lactobacillus*

*casei, Mycobacterium avium* subspecies, *Staphylococcus aureus, Streptococcus* spp., *Enterococcus* spp., or *Entrerobacter* spp.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The invention will hereafter be described by way of the following non-limiting items.

1. A photo bioreactor for pasteurization of liquid food products, e.g. milk, the photo bioreactor including:
    a first cassette mounting frame;
    one or more spiral-shaped tubes extending from an inlet end to an outlet end creating a fluidic pathway;
    at least two cassettes extending from a first end to a second end; and
    one or more filters;
    wherein the cassette mounting frame includes cassette receiving openings into which each of the cassettes are removable mounted,
    wherein each cassette includes one or more light sources illuminating the one or more spiral-shaped tubes, wherein the one or more light sources emit light in a wavelength range between 180-300 nm,
    wherein the one or more filters are positioned between the one or more light sources and the one or more spiral-shaped tubes, and
    wherein the one or more filters prevent light above a wavelength of 300 nm from reaching the one or more spiral-shaped tubes.
2. Photo bioreactor according to item 1, wherein the cassettes are positioned in a parallel configuration.
3. Photo bioreactor according to any preceding item, wherein each cassette also includes one or more of the one or more filters.
4. Photo bioreactor according to any preceding item, wherein one or more of the spiral-shaped tubes are positioned between two of at least two cassettes.
5. Photo bioreactor according to any preceding item, wherein the one or more of the spiral-shaped tubes are grouped in sets of two, such as sets of three, positioned in a configuration alternating between a set of one or more of the spiral-shaped tubes and a cassette.
6. Photo bioreactor according to any preceding item further including a first ventilation chamber positioned at the first end of the one or more cassettes.
7. Photo bioreactor according to any preceding item further including a second ventilation chamber positioned at the second end of the one or more cassettes.
8. Photo bioreactor according to item 6 or 7, wherein the ventilation chamber pulls air out of the cassette or at the ventilation chamber air flows into the cassette.
9. Photo bioreactor according to item 8, wherein the ventilation chamber pulls air out of the cassette at both ends.
10. Photo bioreactor according to item 8, wherein at the ventilation chamber air flows into the cassette at both ends.
11. Photo bioreactor according to item 8, wherein the ventilation chamber pulls air out of the cassette at one end and air flows into the cassette at the other end.
12. Photo bioreactor according to any preceding item, wherein each of the cassettes includes one or more openings at the first end or the second end for insertion and removal of the one or more light sources.
13. Photo bioreactor according to any preceding item, wherein each of the cassettes further includes air intake openings for allowing air to flow into the cassette.
14. Photo bioreactor according to any preceding item, wherein each of the cassettes further includes a cassette frame with openings, wherein a first set of openings are covered by glass, e.g. quartz glass, through which light from the light sources can illuminate the one or more of the spiral-shaped tubes,
15. Photo bioreactor according to item 14, wherein the glass is kept in position inside the cassette frame by a rubber sealing.
16. Photo bioreactor according to item 14 or 15, wherein the one or more filters are coated on or incorporated into the glass.
17. Photo bioreactor according to any preceding item, wherein each of the cassettes further includes a cassette frame with openings, wherein a second set of openings are adapted for facilitating internal air movement inside the cassette.
18. Photo bioreactor according to item 17, wherein the cassette frame includes two or more frame parts arranged in parallel and wherein the second set of openings are positioned in a non-overlapping manner to ensure that light does not escape from the cassette at positions where the light are not illuminating the one or more spiral-shaped tubes.
19. Photo bioreactor according to any preceding item, wherein the cassette a plurality of openings, wherein an air flow is generated through the plurality of openings when a pressure difference is applied between an internal and external surface of the cassette, and wherein flow of air driven by said pressure difference through the plurality of openings provide a uniform cooling along the entire length of the one or more light sources in order to reach maximum UV output and ensure optimum life time of the one or more light sources.
20. Photo bioreactor according to item 19, wherein the openings are designed so light only escape the cassette towards the one or more spiral-shaped tubes.
21. Photo bioreactor according the any preceding item, wherein a space between the cassette and the one or more spiral-shaped tubes are at least partly lined with polished light reflecting aluminum reflecting light from the one or more light sources, such as reflecting at least 70% of the light back towards the one or more spiral-shaped tubes.
22. Photo bioreactor according to any preceding item, further including a plate limiting or avoiding light from the one or more light sources escaping a space between two cassettes in the photo bioreactor.
23. Photo bioreactor according to any preceding item, wherein a space between two cassettes of the photo bioreactor or a space between a cassette and one or more of the spiral-shaped tubes functions as a ventilation shaft used for cooling of the photo bioreactor, especially cooling the cassettes including the one or more light sources.
24. Photo bioreactor according to any preceding item, wherein a fluid movement through the one or more spiral-shaped tubes creates a Dean Vortex flow, laminar flow, or turbulent flow.

25. Photo bioreactor according to any of the preceding items, wherein the one or more spiral-shaped tubes have an inner tube diameter between 1 mm and 10 mm, such as between 2 mm and 9 mm, such as between 3 mm and 8 mm, such as between 4 mm and 7 mm, such as between 5 mm and 6 mm.
26. Photo bioreactor according to any of the preceding items, wherein the one or more spiral-shaped tubes have an inner tube diameter of 5.5 mm.
27. Photo bioreactor according to any of the preceding items, wherein the one or more spiral-shaped tubes have a pitch between 2 and 8 mm, such as between 3 and 7 mm, such as between 4 and 7 mm, such as 6 mm, wherein the pitch is the distance from center to center of the one or more spiral-shaped tubes after one turn/coil of the one or more spiral-shaped tubes.
28. Photo bioreactor according to any of the preceding items, wherein the one or more spiral-shaped tubes have a coil angle between 1 and 6°, such as between 2 and 5°, such as between 3 and 4°, wherein the coil angle is measured between the one or more spiral-shaped tubes and a straight direction compared to the inlet end to the outlet end creating the fluidic pathway.
29. Photo bioreactor according to any of the preceding items, wherein the one or more spiral-shaped tubes have a coil diameter between 20 and 150 mm, wherein the coil diameter is a distance from outer end to outer end of the one or more spiral-shaped tubes after a half turn/coil of the one or more spiral-shaped tubes.
30. Photo bioreactor according to any of the preceding items, wherein the one or more spiral-shaped tubes have an outer tube diameter between 2 and 8 mm, such as between 3 and 7 mm, such as between 4 and 7 mm, such as 6 mm.
31. Photo bioreactor according to any of the preceding items, wherein the one or more spiral-shaped tubes have a wall thickness between 0.1 and 0.4 mm, such as between 0.1 and 0.3 mm, such as between 0.2 and 0.3 mm.
32. Photo bioreactor according to any of the preceding items, wherein the one or more spiral-shaped tubes are coiled around a pillar.
33. Photo bioreactor according to item 32, wherein the pillar is made of a reflective material.
34. Photo bioreactor according to item 33 wherein the pillar is made of a reflective polymeric material.
35. Photo bioreactor according to item 34, wherein the pillar is made of polytetrafluoroethylene (PTFE).
36. Photo bioreactor according to any of the preceding items, wherein the one or more spiral-shaped tubes have a compressed length from the inlet end to the outlet end between 100 mm and 400 mm, wherein the compressed length is the length of the one or more spiral-shaped tubes as shaped in the photo bioreactor without pulling or pressing on the one or more spiral-shaped tubes, so as to get a measure from the inlet to the outlet end.
37. Photo bioreactor according to any of the preceding items, wherein the one or more spiral-shaped tubes have an extension/free length from the inlet end to the outlet end between 5 m and 20 m.
38. Photo bioreactor according to any of the preceding items, wherein the one or more spiral-shaped tubes are made of a polymeric or quartz glass material being ultraviolet light transparent.
39. Photo bioreactor according to item 38, wherein the one or more spiral-shaped tubes are selected from fluorinated ethylene propylene (FEP), polytetrafluoroethylene (PTFE), or perfluoroalkoxy alkanes (PFA).
40. Photo bioreactor according to item 38, wherein the one or more spiral-shaped tubes are from amorphous fluoropolymer (AF).
41. Photo bioreactor according to any of the preceding items, wherein the inlet end and the outlet end is designed such that the liquid food product enters and exits the one or more spiral-shaped tubes axially.
42. Photo bioreactor according to any of the preceding items, wherein the inlet end and the outlet end is designed such that the liquid food product flows overall vertically through the one or more spiral-shaped tubes when observing from inlet end to outlet end.
43. Photo bioreactor according to any of the preceding items 1-41, wherein the inlet end and the outlet end is designed such that the liquid food product flows overall horizontally through the one or more spiral-shaped tubes when observing from inlet to outlet.
44. Photo bioreactor according to any of the preceding items, wherein the one or more light sources are coupled to one or more fibers guiding the 180-300 nm light from the one or more light sources to the one or more spiral-shaped tubes.
45. Photo bioreactor according to item 44, wherein one light source and multiple fibers are used for illuminating the one or more spiral-shaped tubes.
46. Photo bioreactor according to any of the preceding items, wherein the one or more light sources are selected from a mercury-vapor lamp, xenon lamp, or a light emitting diode (LED).
47. Photo bioreactor according to any of the preceding items, wherein the one or more light sources are a low pressure germicidal lamp, such as a low-pressure mercury-vapor lamp.
48. Photo bioreactor according to any of the preceding items, wherein the one or more light sources operate at a lamp temperature between 0° C. and 120° C., such as between 20° C. and 60° C., such as between 30° C. and 50° C.
49. Photo bioreactor according to any of the preceding items, wherein the one or more filters are selected from band-pass filters, notch filters, or a combination of both.
50. Photo bioreactor according to any of the preceding items further including a reactor housing.
51. Photo bioreactor according to item 50, wherein the one or more spiral-shaped tubes, the cassettes, and the one or more filters are enclosed inside the reactor housing.
52. Photo bioreactor according to item 50 or 51, wherein the reactor housing is made of a UV-C reflective material.
53. Photo bioreactor according to items 50-52, wherein the reactor housing is made of reflective polytetrafluoroethylene (PTFE).
54. Photo bioreactor according to any of the preceding items, wherein the photo bioreactor further includes a control unit, wherein the control unit includes electronic temperature control and flow control.
55. Photo bioreactor according to item 54, wherein the control unit automatically controls the lamp temperature and a flow speed of a liquid through the fluidic pathway.
56. Use of a photo bioreactor according to any of the items 1-55 for cold pasteurization of liquid food products.

57. Use of a photo bioreactor according to any of the items 1-55 for killing microorganisms in liquid food products, such as bacteria, mold, spores, or virus.
58. Use of a photo bioreactor according to item 56 or 57, wherein the liquid food products are selected from liquid dairy products.
59. Use of a photo bioreactor according to item 56 or 57, wherein the liquid food products are selected from raw milk, milk, juice, coffee, tea, soya, soylent, soda, broth, soup, beer, smoothies, protein shake, liquid meal-replacement, cream, wine, mayonnaise, ketchup, syrup, honey, or opaque processing water.
60. Use of a photo bioreactor according to item 56 or 59, wherein a biological contaminant is inactivated or reduced by an order of at least 2-$Log_{10}$, such as at least 3-$Log_{10}$, such as at least 4-$Log_{10}$, such as at least 5-$Log_{10}$, such as at least 6-$Log_{10}$.
61. Use of a photo bioreactor according to item 60, wherein the biological contaminant is selected from *Campylobacter jejuni*, *Shigella*, *Coxiella burnetii*, *Escherichia coli*, *Listeria monocytogenes*, *Mycobacterium bovis*, *Mycobacterium tuberculosis*, *Mycobacterium paratuberculosis*, *Salmonella* spp., *Yersinia enterocolitica*, *Brucella* spp., *Staphylococcus* spp., *Lactobacillus casei*, *Mycobacterium avium* subspecies, *Staphylococcus aureus*, *Streptococcus* spp., *Enterococcus* spp., or *Entrerobacter* spp.

BRIEF DESCRIPTION OF THE DRAWINGS

FIG. 2 shows an end view of the first embodiment of the present invention showing a cassette.

FIG. 3 shows section A-A of FIG. 2.

DETAILED DESCRIPTION OF THE INVENTION

FIGS. 1, 2, 3 and 4 show one embodiment of the present invention. In the embodiment multiple cassettes 1 are placed parallel to each other with gaps to fit the one or more spiral-shaped tubes 2. The spiral-shaped tubes 2 may be made of Teflon. The liquid to be pasteurized flows through the spiral-shaped tubes 2, while the spiral-shaped tubes are mounted on a polished stainless steel pillar 3 that reflects UV light passing through the liquid and gaps between in the spiral-shaped tubes. Fittings 4 are mounted at the ends of the spiral-shaped tubes 2 to connect an input and an output. This setup allows modularity and easy access for assembly and maintenance of the system. A sheet metal shielding 5 is used for blocking UV from escaping the chamber and is combined in a system with the spiral-shaped tubes 2 and the polished stainless steel pillar 3 to allow it to be pulled out in conjunction for inspection and maintenance.

Figure 1:
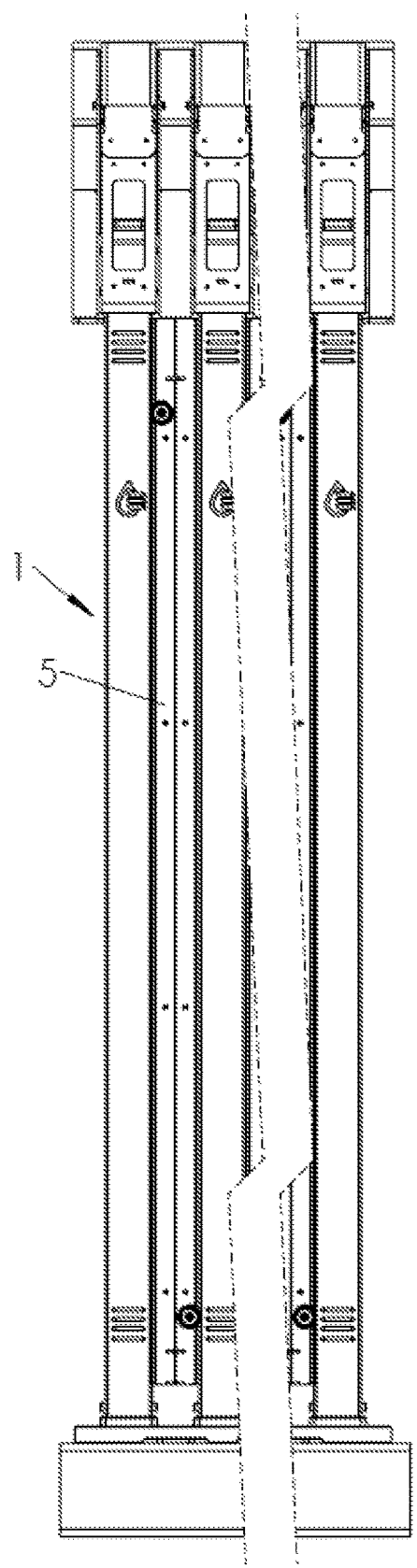
FIG. 1 shows a side view of a first embodiment of the present invention showing cassettes.
Figure 4:
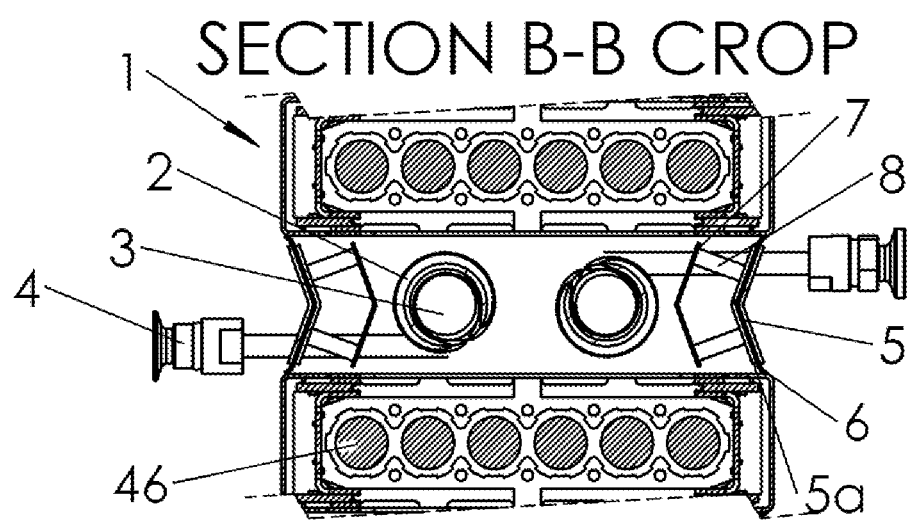
FIG. 4 shows section B-B of FIG. 2.

FIG. 4 shows the section B-B from FIG. 2. Two pieces of sheet metal shielding 5 and 5*a* are used to compress a rubber sealant 6 and together create an enclosure that gets between cassettes to block UV light from escaping the system and create a chamber for more efficient air movement for cooling the system. A polished sheet metal plate 7 reflects more UV light to coils. Spacers 8 are used to attach the polished sheet metal plate 7 to the two pieces of sheet metal shielding 5 and 5*a* and the rubber sealant 6. The spacers 8 further helps to position the polished sheet metal plate 7 at the correct distance, which may be based on calculation, from the spiral-shaped tubes 2 to obtained the most efficient performance. The figure further shows the light source 46, such as UV lamps, inside the cassette 1.

Figure 5:
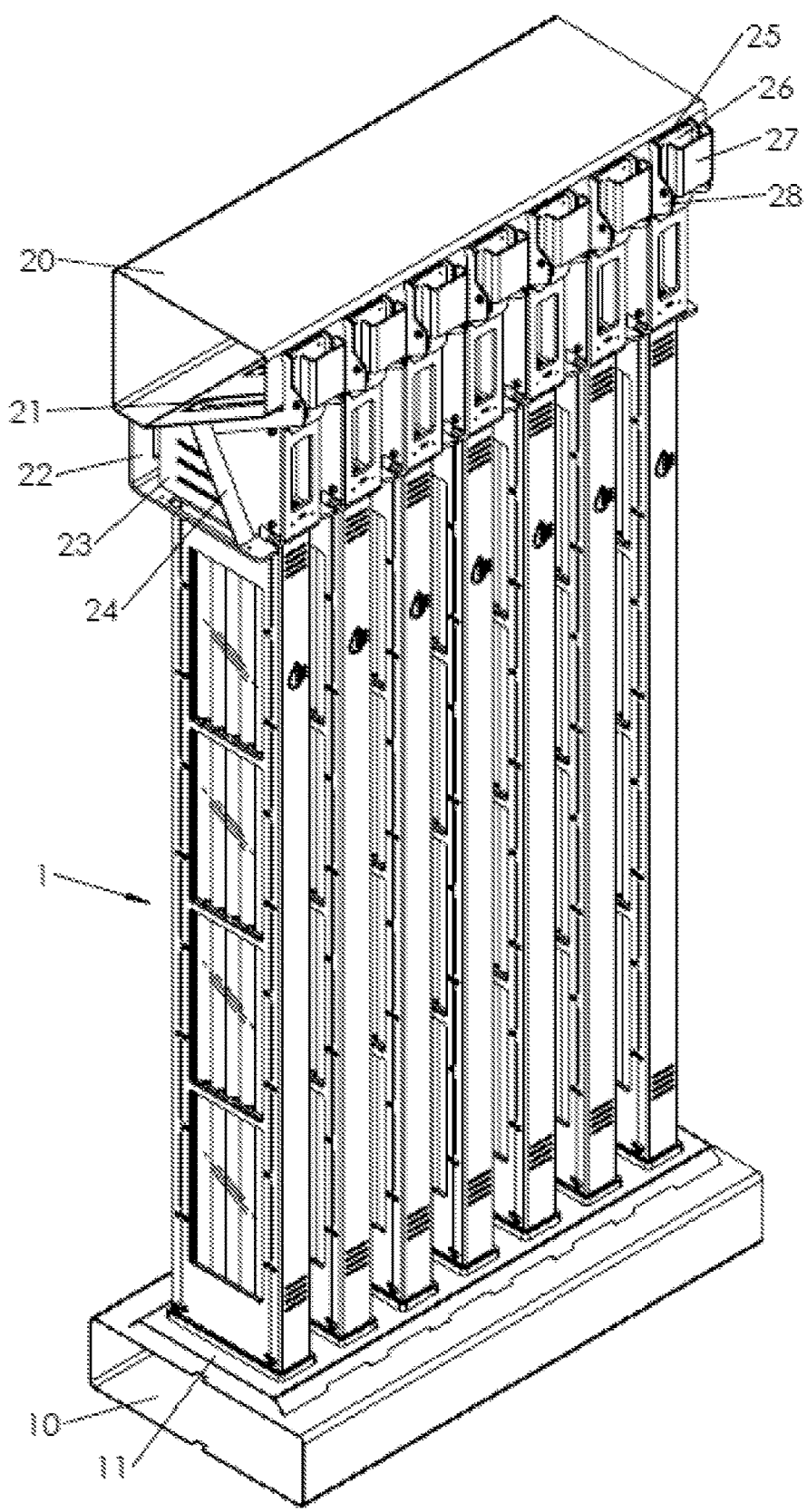
FIG. 5 shows a slightly turned birds-eye view of another embodiment of the present invention in which cassettes are mounted in the system.

FIG. 5 shows another embodiment of the present invention in which the cassettes 1 are mounted into a bottom ventilation chamber 10 through which air is being sucked out at the ends. A cassette mounting frame 11 holds cassettes in place. The embodiment further includes a top ventilation chamber 20 through which air is being sucked out at the ends. A gasket 21 between cassette 1 and top ventilation chamber 20 creates a seal. Sheet metal parts 22, 23, and 24 with cut-outs for air movement are used to guide and keep cassettes 1 in place, while a plastic tongue spacer 25 is used to hold cassette 1 in place. Another sheet metal part 26 is used to hold cassette 1 in place, while a handle 27 is used to move the plastic tongue spacer 25 and the sheet metal part 26 up and down using gear-like cut-outs to release and lock the cassette 1 in place. A sheet metal plate 28 is welded on the top ventilation chamber 20 to keep the plastic tongue spacer 25, the sheet metal part 26, and the handle 27 in place.

Figure 6:
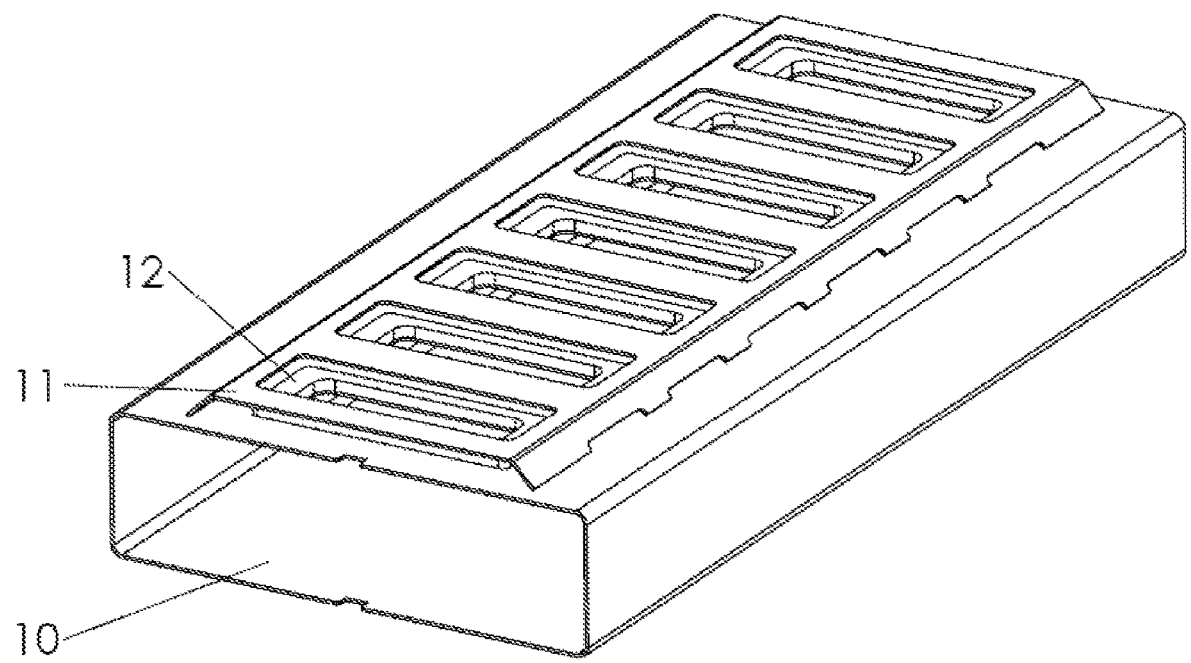
FIG. 6 shows a slightly turned birds-eye view of a bottom ventilation chamber according to an embodiment of the present invention.

FIG. 6 shows a bottom ventilation chamber 10 according to an embodiment of the present invention. The bottom ventilation chamber 10 have rectangular holes where cassettes are joined using gaskets 12 to create a seal. Air is can be sucked out at the ends. A cassette mounting frame 11 is welded to the bottom ventilation chamber 10 to keep the cassettes in place.

Figure 7:
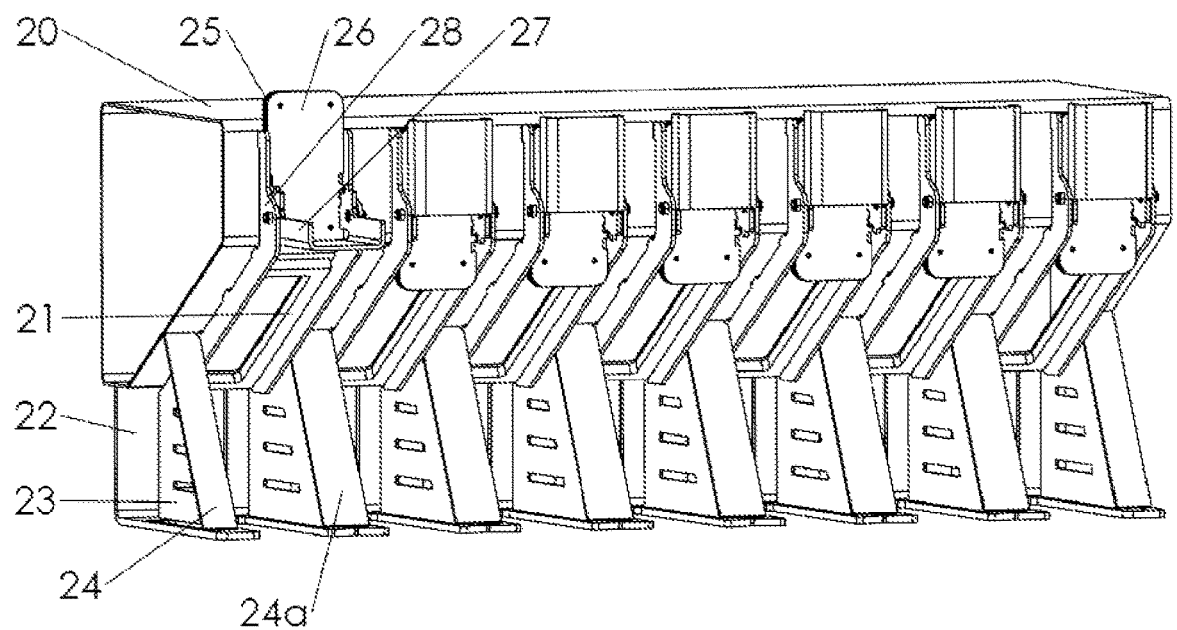
FIG. 7 shows a slightly turned side view of a part of a top ventilation chamber according to an embodiment of the present invention.

FIG. 7 shows part of a top ventilation chamber according to an embodiment of the present invention. A plastic tongue spacer 25 and a sheet meal part 26 is in an up-wards position when a handle 27 is pulled down hereby unlocking and allowing easy installation and removal of the cassette. The figure further shows a gasket 21, other sheet metal parts 22, 23, 24, and 24a, and a sheet metal plate 28.

Figure 8:
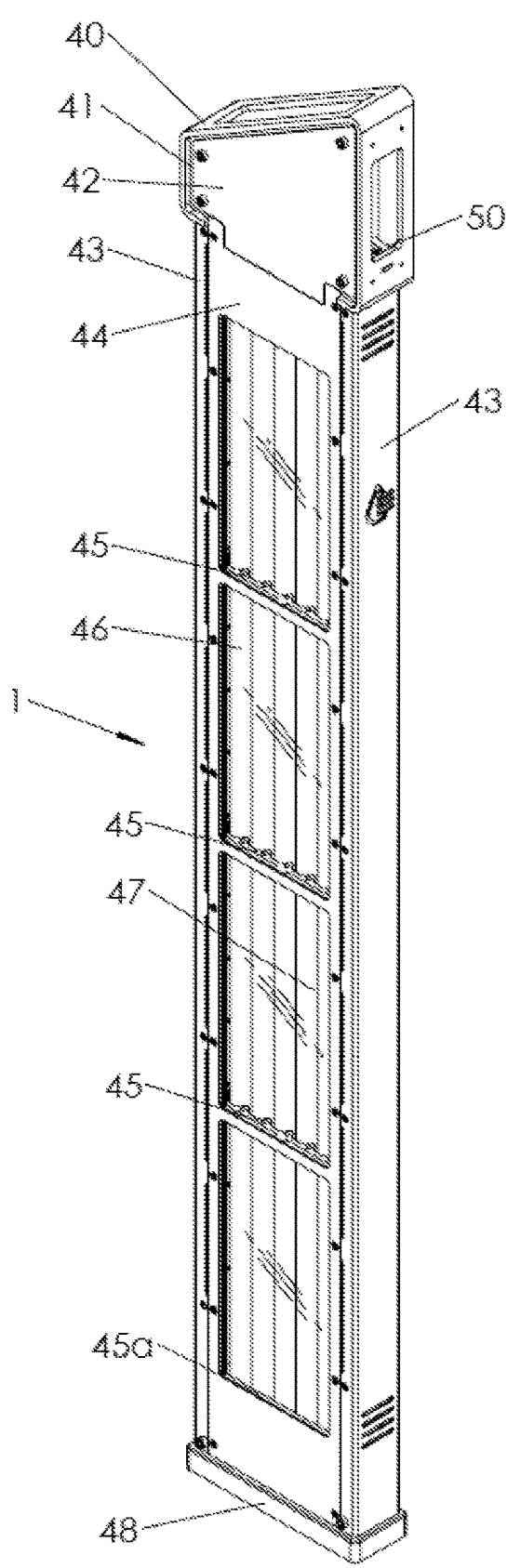
FIG. 8 shows a slightly turned birds-eye view of a cassette according to an embodiment of the present invention

FIG. 8 shows a cassette 1 according to an embodiment of the present invention. The cassette 1 includes a sheet metal part 40 with cut-outs for air movement and insertion of a light source 46, such as UV lamps, another sheet metal part 41 includes threaded holes, which are used to hold a sheet metal cover 42 that is placed after installing the wires for the light source 46. The cassette 1 further includes a sheet metal part 43 with multiple cut-outs for air intake into the cassette and which aid in blocking UV light hereby evading UV light in escaping the cassette 1. The cassette 1 further includes a sheet metal plate 44 with multiple cut-outs used to hold quartz glass 47 in place. A sheet metal part 45 is used to guide and hold the light source 46, to separate quartz glasses 47, to create gaps for extra air intake, and to generate vortex inside the cassette chamber. A further sheet metal part 45a used to hold the bottom part of the quartz glass 47 in place. This sheet metal part 45a has wider internal cut-outs than the other sheet metal part 45, to facilitate that air is being sucked out at the bottom of cassette 1. The quartz glass 47 is used to keep the heat from the light source 46 inside the cassette 1, hereby allowing it to be sucked out in top and/or bottom of the cassette 1. The quartz glass 47 may further include the filter used to block of any unwanted wavelength. A plastic part 48 is used to hold the light sources 46 in position. The design of this particular embodiment creates a faster air movement at the end of the light sources, which has the highest temperature during operation. The plastic part 48 creates a seal using the gasket 12 from the embodiment of FIG. 6 and allows efficient air suction through the bottom ventilation chamber 10 from the embodiment of FIG. 6.

Figure 9:
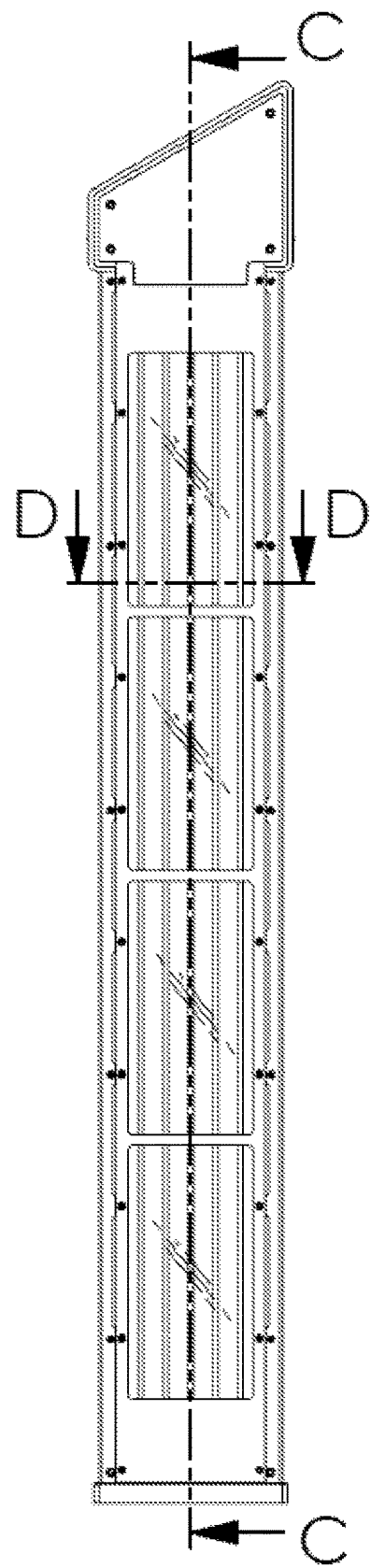
FIG. 9 is showing a side view of the embodiment as disclosed in FIG. 8.

FIG. 9 is showing a side view of the embodiment as disclosed in FIG. 8.

Figure 10:
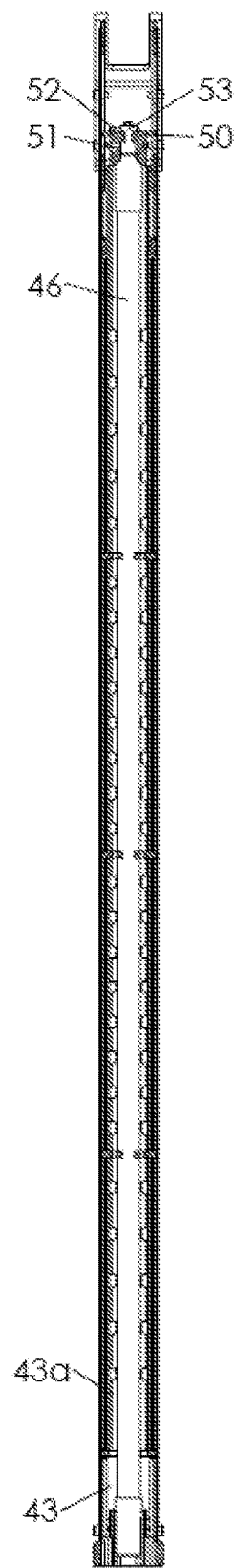
FIG. 10 shows section C-C of FIG. 9.

FIG. 10 shows the section C-C of FIG. 9. The cassette includes a sheet metal part 43 with multiple cut-outs for air intake into the cassette. The sheet metal part 43 is further used for blocking UV light hereby preventing it from escaping the cassette. Another sheet metal part 43a comprises cut-outs wherein the size of the cut-outs are based on calculation. The sheet metal part 43a is used for evenly distributed cooling of the light sources 46. The cut-outs or the sheet metal part 43a are not aligning with the cut-outs of the sheet metal part 43, hereby allowing air movement through the cut-outs but blocking UV light hereby preventing light from escaping the cassette. A further sheet metal part 50 is used to hold a milled plastic part that is holding a ceramic light source pin connector 53, while a locking part 52 is locking the milled plastic part 51 in place.

Figure 11:
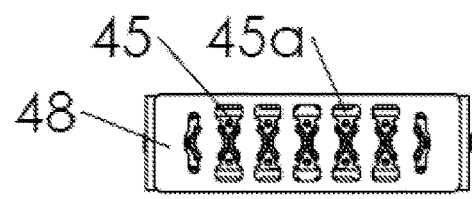
FIG. 11 shows a bottom view of the cassette of the embodiment as disclosed in FIGS. 8, 9, and 10.

FIG. 11 shows a bottom view of the cassette of the embodiment as disclosed in FIGS. 8, 9, and 10, showing the sheet metal parts 45 and 45a, and showing the plastic part 48 where the cut-outs are visible.

Figure 12:
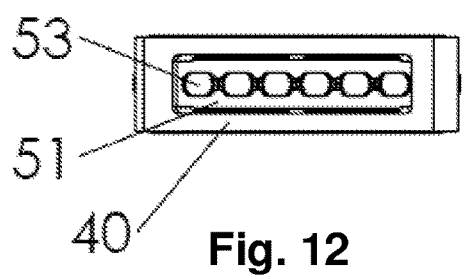
FIG. 12 shows a top view of the cassette of the embodiment as disclosed in FIGS. 8, 9, 10, and 11.

FIG. 12 shows a top view of the cassette of the embodiment as disclosed in FIGS. 8, 9, 10, and 11, showing the sheet metal part 40, the milled plastic part 51, and the ceramic light source pin connector 53.

Figure 13:
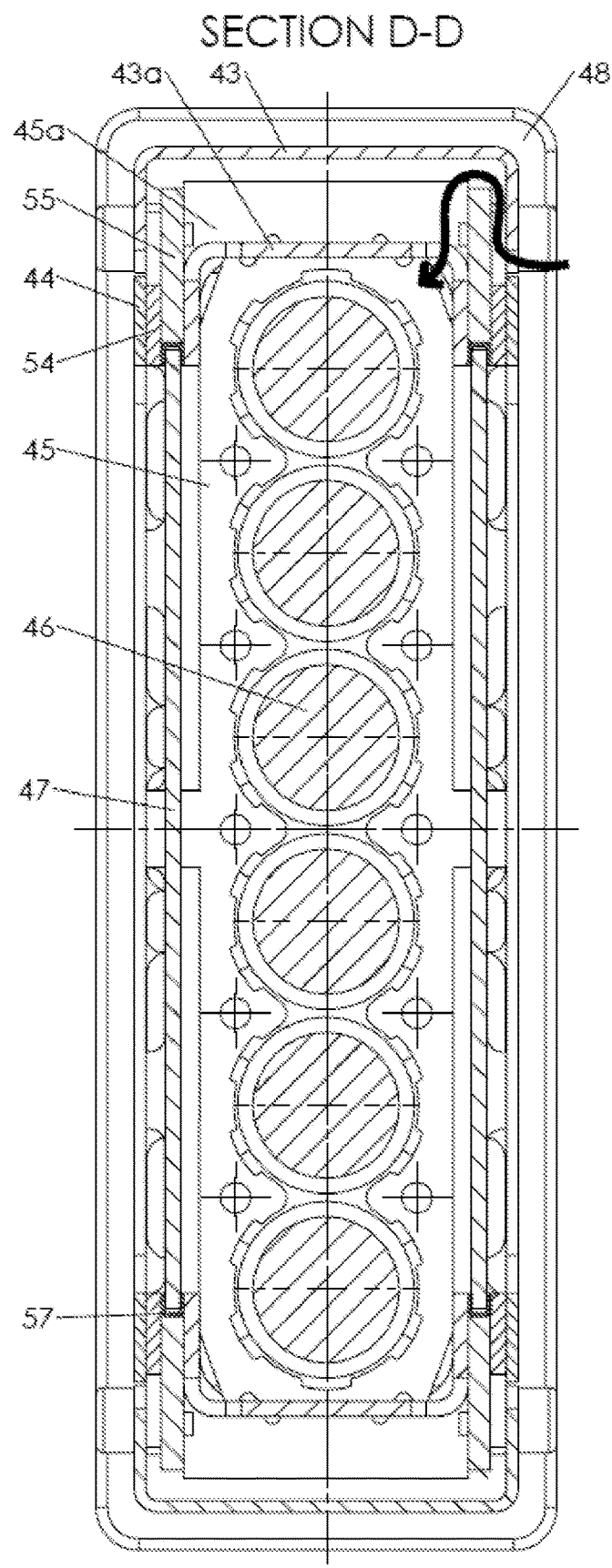
FIG. 13 shows the section D-D of FIG. 9.

FIG. 13 shows the section D-D of FIG. 9. FIG. 13 shows a rubber sealing 57 that positions quartz glass 47 between the sheet metal part 43a and another sheet metal part 54. The figure shows an additional sheet metal part located at the sides of the quartz glass 47. The thick black arrow shows air movement that is being sucked into a cassette between the sheet metal parts 43, 44, 54, and 55. The figure further shows the sheet metal parts 45a and 45, the light source 46, and the plastic part 48, all as disclosed in FIGS. 8, 9, 10, 11, and/or 12.

Figure 14:
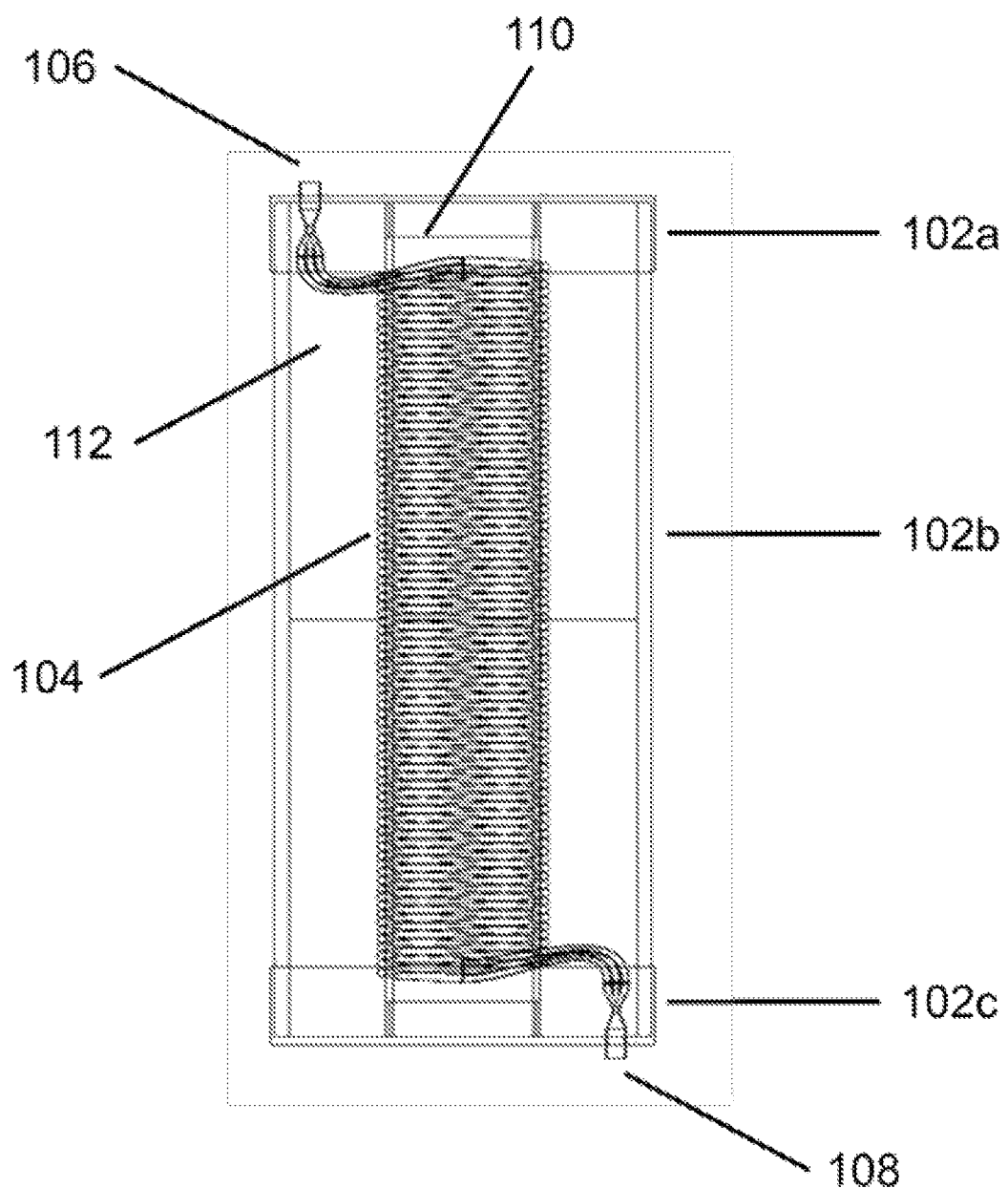
FIG. 14 shows a see-through front view of an embodiment of the present invention, showing a reactor housing, a spiral-shaped tube comprising an inlet and an outlet, a pillar, and a filter.
Figure 15:
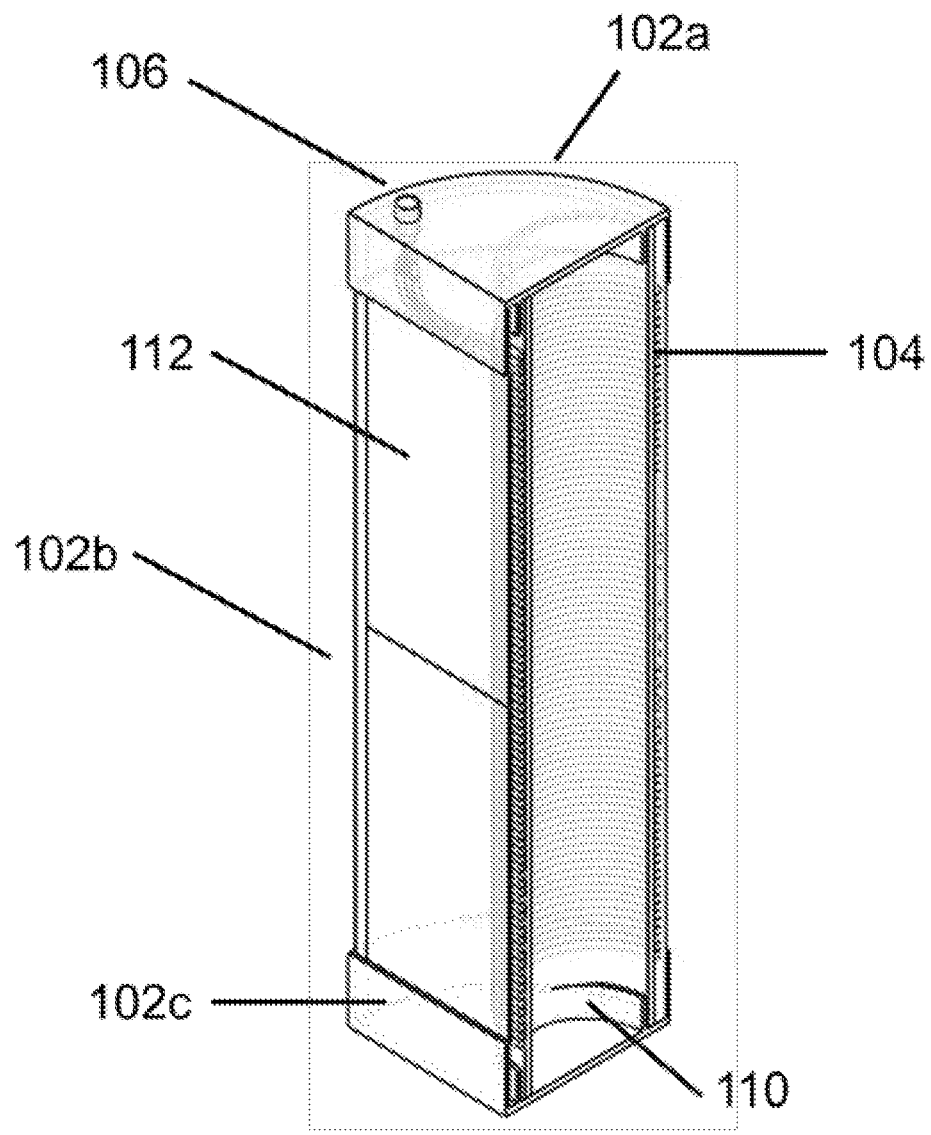
FIG. 15 shows a cut-through side view of an embodiment of the present invention, showing a reactor housing, a spiral-shaped tube comprising an inlet and an outlet (not shown), a pillar, and a filter. The cut is made down the middle of the reactor housing.

The FIGS. 14 and 15 shows different views of an embodiment of a photo bioreactor for cold pasteurization of liquid food products. The photo bioreactor includes a spiral-shaped tube 104 extending from an inlet end 106 to an outlet end 108 creating a fluidic pathway. The spiral-shaped tube 104 is coiled around a pillar 110.

The photo bioreactor further includes a reactor housing 102a, 102b, 102c, which comprises three parts; a first part 102a positioned on the top of the photo bioreactor, a second part constituting the side of the housing, and a third part positioned at the lower side of the photo bioreactor. In this embodiment the reactor housing is round shaped on one side, however, it may also be other shapes such as square.

A filter 112 positioned between outside the spiral-shaped tube 104 is also shown. The filter 112 prevents light above a wavelength of 300 nm from reaching the spiral-shaped tube 104.

The filter 112 is shown as see-through filter in FIG. 14. In FIG. 15, the shown cut is made down the middle of the reactor housing 102a, 102b, and 102c.

The photo bioreactor shown in FIGS. 14 and 15 are examples of photo bioreactors where the liquid food product flows overall vertically through the one or more spiral-shaped tube 104 when observing from inlet end 106 to outlet end 108.

Figure 16:
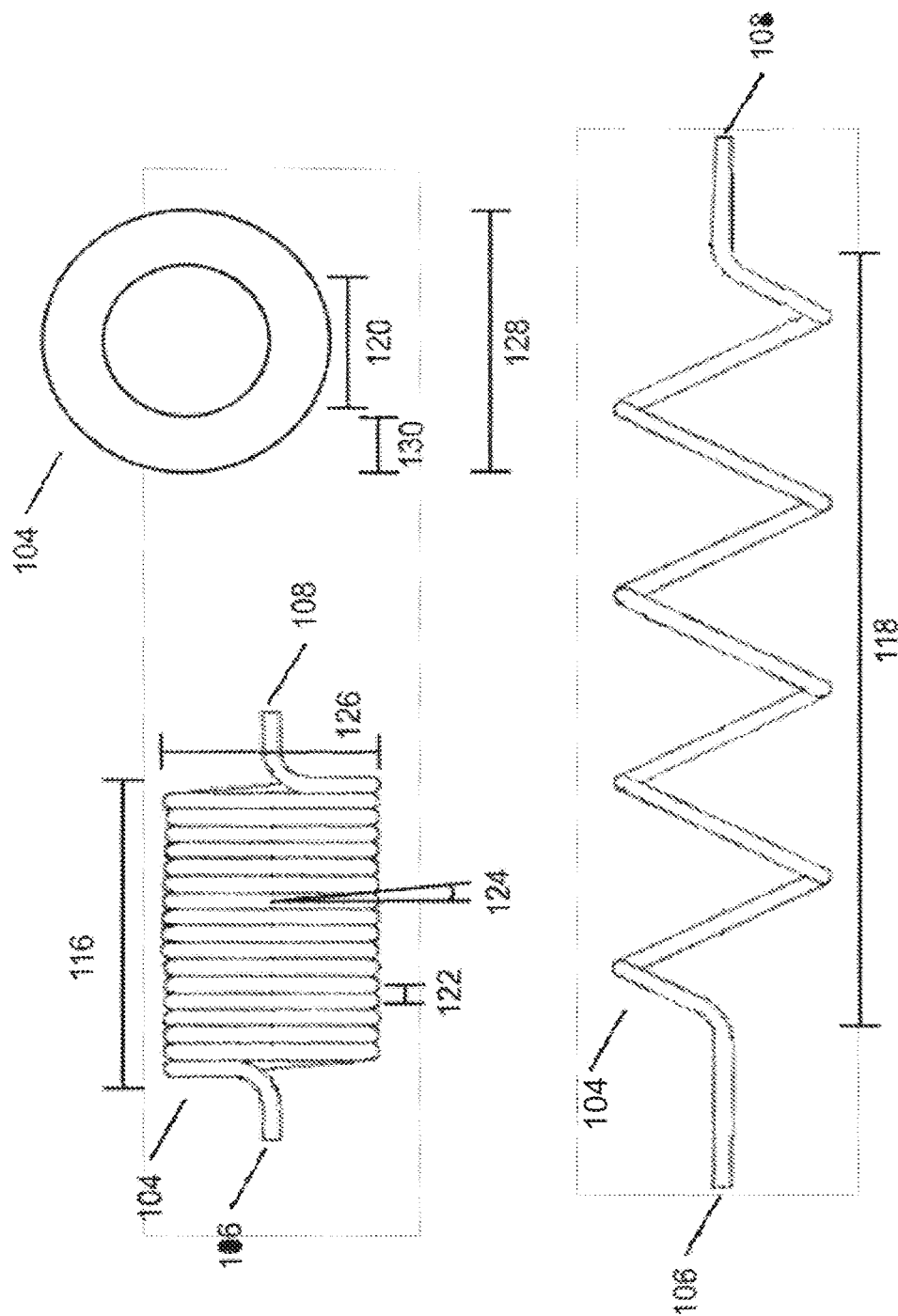
FIG. 16 shows a schematic illustration of different parts and measurements of specific embodiments of the present invention.

FIG. 16 shows spiral-shaped tubes 104 with inlet 106 and outlet 108 according to the invention. The compressed length of the spiral-shaped tube 116, the extension/free length of the spiral-shaped tubes 118, the inner tube diameter 120, the pitch 122, the coil angle 124, the coil diameter 126, the outer tube diameter 128, and the wall thickness 130 are all illustrated in FIG. 16.

Figure 17:
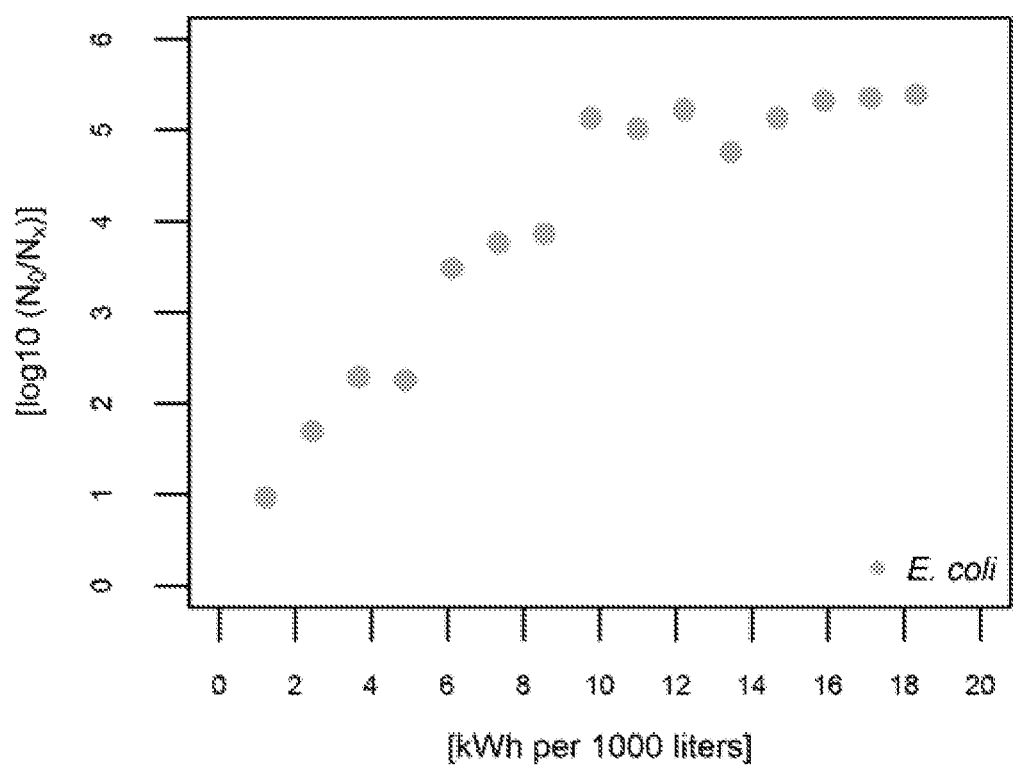
FIG. 17 shows an investigation of the amount of energy required from the light source to obtain inactivation or reduction of the biological contaminant.

FIG. 17 shows the investigation of the amount of energy required from the light source to obtain inactivation or reduction of the biological contaminant.

Figure 18:
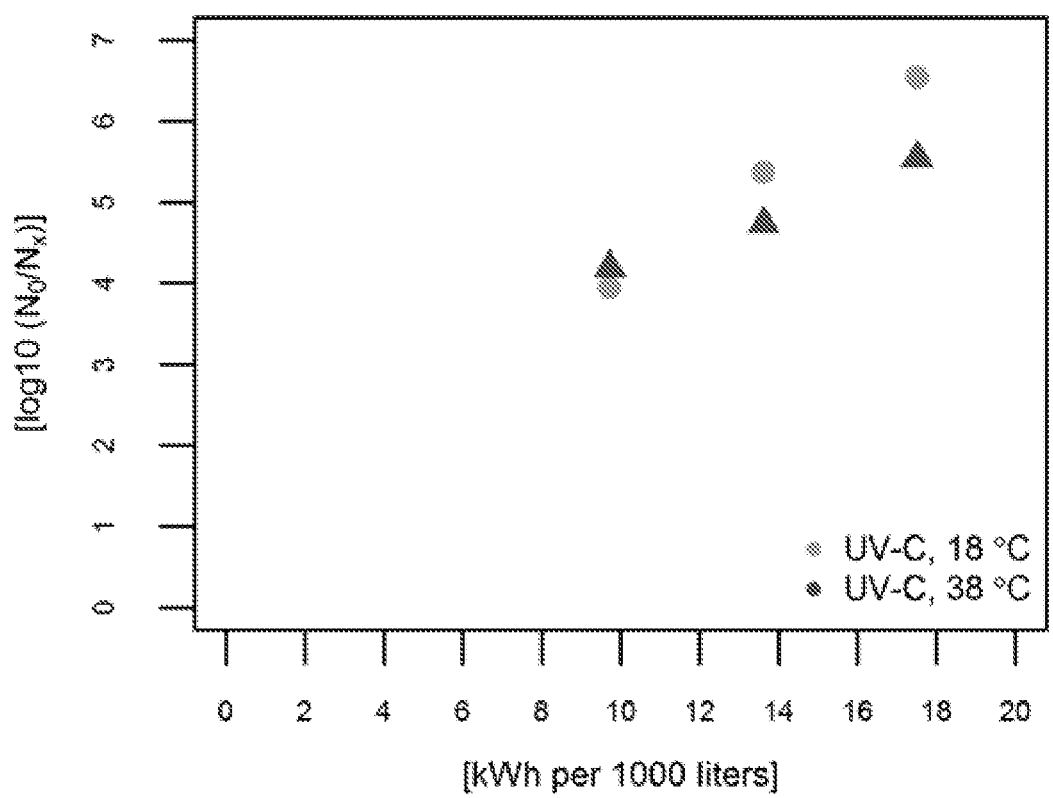
FIG. 18 shows an investigation of the difference in the current invention when varying the temperature from 18 degrees centigrade to 38 degrees centigrade.

FIG. 18 shows the investigation of the difference in the current invention when varying the temperature from 18 degrees centigrade to 38 degrees centigrade.

Figure 19:
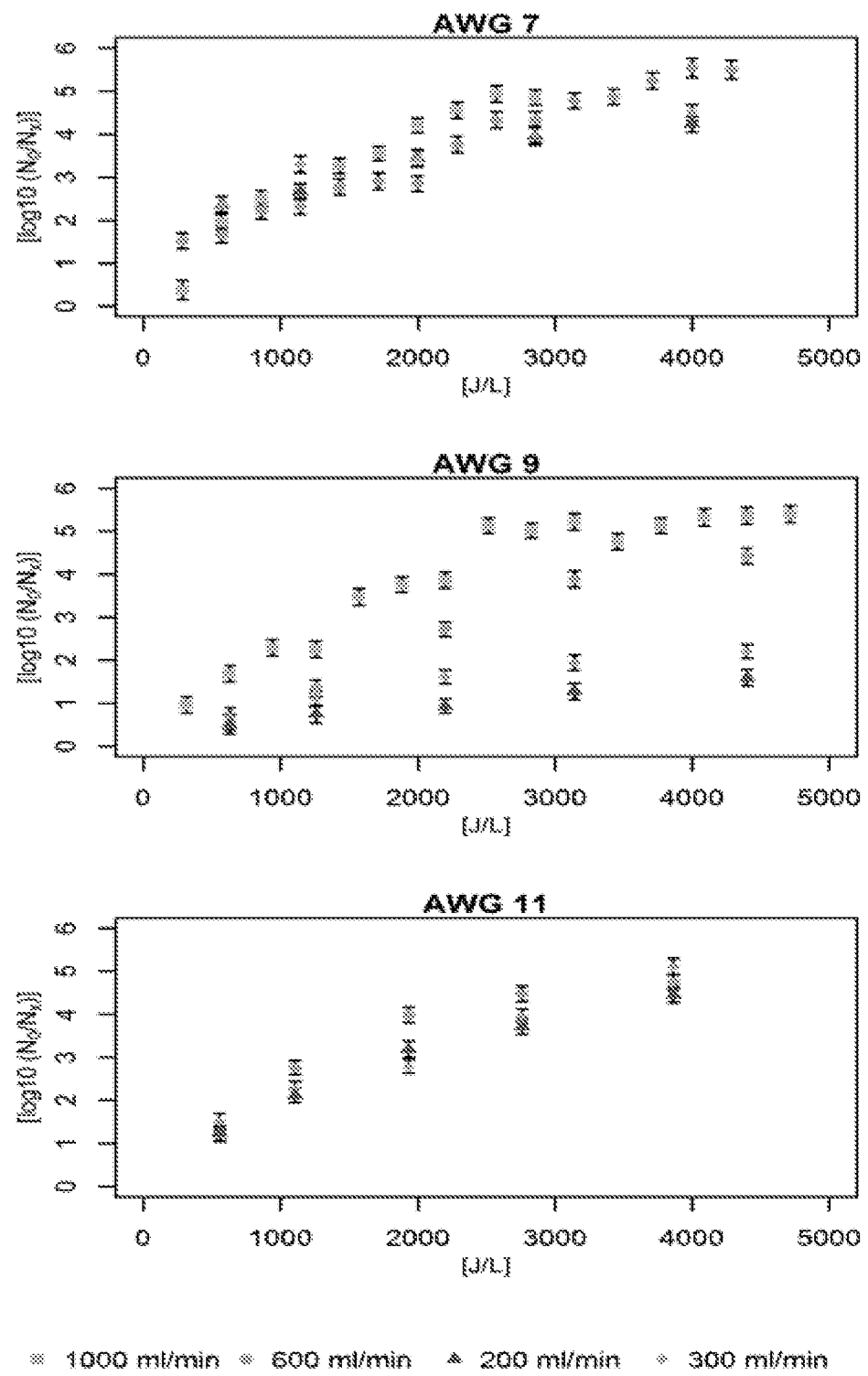
FIG. 19 shows an investigation of the current invention when varying the flow rate of the liquid at three different tube sizes.

FIG. 19 shows the investigation of the current invention when varying the flow rate of the liquid at three different tube sizes.

Figure 20:
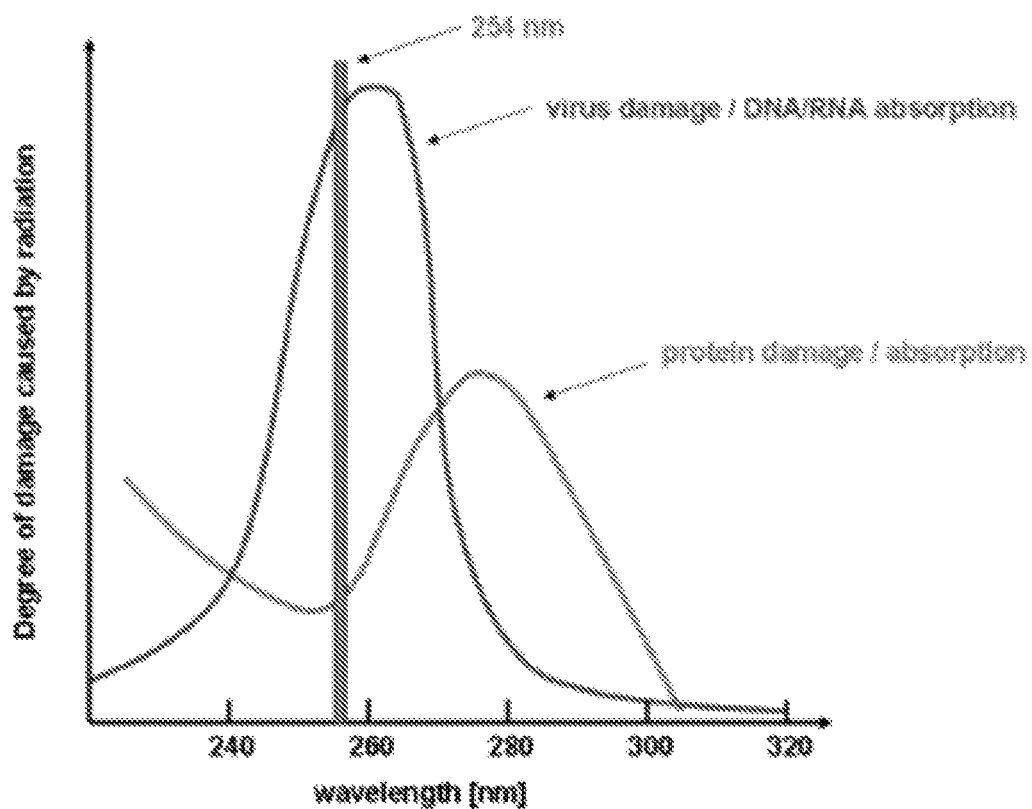
FIG. 20 shows a degree of damages caused by radiation in virus versus protein at different wavelengths (220-320 nm).

FIG. 20 shows the degree of damages caused by radiation in virus versus protein at different wavelengths (220-320 nm).

EXAMPLES

General Experimental Procedure

The effects of tube diameter and flow rate were investigated using UHT whole milk spiked with *Escherichia coli* to a concentration of minimum $2.7 \times 10^6$ per milliliter (determined using the most probable number method).

One liter litre UHT whole milk were transferred to a sterilized blue cap flask and added 1 ml of *Escherichia coli* media, achieving a desired minimum concentration of at least $2.7 \times 10^6$/ml. The spiked milk was circulated in the UV-reactor and samples were taken at intervals, when desired UV-C doses were achieved. The spiked milk was mixed constantly throughout the experiment using a magnetic stirrer.

For each specific flowrate and tube size a new batch of 1 litre UHT whole milk spiked with *Escherichia coli* to a minimum concentration of 2.7E6/ml was prepared.

The UV-reactor consisted of a FEP tube coiled around a 28 mm quartz glass. Within the quartz glass a 75 W germicidal lamp with a peak radiation at 253.7 nm was placed. The tested tube sizes were AWG (American wire gauge) 7, 9, and 11 and the flowrates investigated were 200, 300, 600 and 1000 ml per minute.

The milk was circulated using a rotary vane pump and exposed in the UV-reactor for a period of time before samples of 20 ml were taken using sterilized pipettes and transferred to a sterilized blue cap flask. The milk was circulated in the system, with the lamp off prior to each experiment and a sample was taken to establish the start concentration. The milk temperature was 24 to 25° C. at the start of each experiment and 34 to 43° C. at the end of each experiment.

After each experiment, the system went through a CIP (clean-in-place) procedure, first flushing the system using demineralised water for 10 minutes, followed by 40 minutes of circulating a 1% NaOH solution at 65° C. Followed by flushing the system for 10 minutes using demineralised water. After which a 0.5% $HNO_3$ solution at 60° C. were circulated in the system for 40 minutes. Finally, the system was rinsed for 20 minutes using demineralised water.

The samples were transferred to a sampling station in a laminar biosafety cabinet immediately after the experiment ended, where they were treated using the MPN method following Jarvis et al. [Jarvis, B. et al., Journal of Applied Microbiology, 2010, 109, 1660-1667].

After two days in an incubator at 35° C. the number of positive test tubes was counted and the bacteria concentrations calculated.

Example 1

Experimental example 1 investigates the amount of energy required from a pump and the light source to obtain inactivation or reduction of the biological contaminant. The tested tube size is AWG 9 and the flowrate investigated is 700 ml per minute. As can be seen in FIG. 17, by using a small amount of light energy (around 1.2 kWh per 1,000 liter liquid) a 1-$Log_{10}$ reduction is obtained. When increasing the light energy used the $Log_{10}$ reduction is also increasing until a plateau is obtained from 10 kWh per 1,000 liter liquid with a reduction of around 5-Logo.

Example 2

Experimental example 2 investigates the difference in the current invention when varying the temperature from 18 degrees centigrade to 38 degrees centigrade. The tested tube size is AWG 9 and the flowrate investigated is 700 ml per minute. As shown in FIG. 18, the difference in $log_{10}$ reduction is similar around 10 kWh per 1,000 liter liquid. However, when the energy used is increased, the $log_{10}$ reduction between 18 degrees centigrade and 38 degrees centigrade start to be significant. At energies of around 18 kWh per 1,000 liter liquid the $log_{10}$ reduction is 5.5 for 38 degrees centigrade, while it is 6.5 for 18 degrees centigrade, which corresponds to 1-$log_{10}$ reduction in difference.

Example 3

Experimental example 3 investigates the current invention when varying the flow rate of the liquid at three different tube sizes. The tested tube sizes were AWG 7, 9, and 11 and the flowrates investigated were 200, 300, 600 and 1000 ml per minute. The temperature is kept between 24 and 43 degrees centigrade. As can be observed in FIG. 19, depending on the tube size, the setup is optimal at different flowrates.

Using a tube size of AWG 7 there is a small difference between flowrates. However, this difference is most predominant when analyzing at high energy exposure (around 4,000 J per liter liquid) where a 1-$log_{10}$ difference is observed between flowrates of 200-300 ml/min versus flowrates of 600-1,000 ml/min.

Using a tube size of AWG 9 there is a large difference between flowrates. This difference is largest when analyzing at high energy exposure (around 4,500 J per liter liquid) where a 3-$log_{10}$ difference is observed between flowrates of 200-300 ml/min versus flowrates of 600-1,000 ml/min.

Using a tube size of AWG 11 there is a very small difference between flowrates. However, this difference is negligible when analyzing at high energy exposure (around 4,000 J per liter liquid).

REFERENCES

1—Cassette
2—Spiral-shaped tube
3—Polished stainless steel pillar
4—Fitting
5, 5a—Sheet metal shielding
6—Rubber sealant
7—Polished sheet metal plate
8—Spacer
10—Bottom ventilation chamber
11—Cassette mounting frame
12—Gasket
20—Top ventilation chamber
21—Gasket
22, 23, 24, 24a, 26, 40, 41, 43, 43a, 45, 45a, 50, 54, 54—Sheet metal part
25—Plastic tongue spacer
27—Handle
28, 44—Sheet metal plate
42—Sheet metal cover
46—Light source
47—Quartz glass
48—Plastic part
51—Milled plastic part
52—Locking part
53—Ceramic light source pin connector
57—Rubber sealing
102a—First part of reactor housing
102b—Second part of reactor housing
102c—Third part of reactor housing
104—Spiral-shaped tubes
106—Inlet
108—Outlet
110—Pillar
112—Filter
116—Compressed length
118—extension/free length
120—Inner tube diameter
122 Pitch
124 Coil angle
126 Coil diameter
128 Outer tube diameter
130 Wall thickness

The invention claimed is:

1. A photo bioreactor for pasteurization of a liquid food product, the photo bioreactor comprising:
   a cassette mounting frame;
   one or more spiral-shaped tubes extending from an inlet end to an outlet end creating a fluidic pathway;
   at least two cassettes extending from a first end to a second end; and
   one or more filters;
   wherein the cassette mounting frame has cassette receiving openings into which each of the at least two cassettes are removably mounted,
   wherein each of the at least two cassettes comprises one or more light sources-illuminating the one or more spiral-shaped tubes, wherein the one or more light sources emit light in a wavelength range between 180-300 nm,
   wherein one or more of the one or more spiral-shaped tubes are positioned between two of the at least two cassettes and do not surround either of the two of the at least two cassettes,
   wherein the one or more filters are positioned between the one or more light sources and the one or more spiral-shaped tubes, and
   wherein the one or more filters prevent light above a wavelength of 300 nm from reaching the one or more spiral-shaped tubes.

2. The photo bioreactor according to claim 1, wherein the at least two cassettes are positioned in a parallel configuration.

3. The photo bioreactor according to claim 1, wherein each of the at least two cassettes also comprises one or more of the one or more filters.

4. The photo bioreactor according to claim 1, wherein the one or more of the one or more spiral-shaped tubes are grouped in sets of two or sets of three, positioned in a configuration alternating between a set of one or more of the spiral-shaped tubes and one of the at least two cassettes.

5. The photo bioreactor according to claim 1, further comprising:
   a first ventilation chamber positioned at the first end of the at least two cassettes and/or a second ventilation chamber positioned at the second end of the at least two cassettes, wherein the first ventilation chamber and the second ventilation chamber pull air out of the at least two cassettes or the first ventilation chamber and the second ventilation chamber have air flow into the at least two cassettes or the first ventilation chamber and the second ventilation chamber pull air out of the at least two cassettes at both ends or at the first ventilation chamber and the second ventilation chamber air flows into the at least two cassettes at both ends or the first ventilation chamber and the second ventilation chamber pull air out of the at least two cassettes at one end and air flows into the at least two cassettes at the other end.

6. The photo bioreactor according to claim 1, wherein each of the at least two cassettes comprises one or more openings at the first end or the second end for insertion and removal of the one or more light sources, wherein each of the at least two cassettes further comprises air intake openings for allowing air to flow into the at least two cassettes.

7. The photo bioreactor according to claim 1, wherein each of the at least two cassettes further comprises a cassette frame with a set of openings covered by glass through which light from the one or more light sources can illuminate the one or more spiral-shaped tubes.

8. The photo bioreactor according to claim 7, wherein the one or more filters are coated on or incorporated into the glass.

9. The photo bioreactor according to claim 7, wherein the cassette frame of each of the at least two cassettes further comprises a second set of openings adapted for facilitating internal air movement inside the at least two cassettes.

10. The photo bioreactor according to claim 9, wherein the cassette frame of each of the at least two cassettes comprises two or more frame parts arranged in parallel and wherein the second set of openings are positioned in a non-overlapping manner to ensure that light does not escape from each of the at least two cassettes at positions where the light is not illuminating the one or more spiral-shaped tubes.

11. The photo bioreactor according to claim 1, wherein each of the at least two cassettes comprises a plurality of openings, wherein an air flow is generated through the plurality of openings when a pressure difference is applied between an internal surface and an external surface of each of the at least two cassettes, and wherein flow of air driven by the pressure difference through the plurality of openings provides a uniform cooling along an entire length of the one or more light sources in order to reach maximum UV output and ensure optimum life time of the one or more light sources.

12. The photo bioreactor according to claim 11, wherein the plurality of openings are designed so light only escapes each of the at least two cassettes towards the one or more spiral-shaped tubes.

13. The photo bioreactor according to claim 1, wherein a space between the at least two cassettes and the one or more spiral-shaped tubes is at least partly lined with polished light reflecting aluminum reflecting light from the one or more light sources back towards the one or more spiral-shaped tubes.

14. The photo bioreactor according to claim 1, further comprises a plate limiting or preventing light from the one or more light sources escaping a space between the at least two cassettes.

15. The photo bioreactor according to claim 1, wherein a space between the at least two cassettes-functions as a ventilation shaft used for cooling of the photo bioreactor, including the at least two cassettes comprising the one or more light sources.

16. The photo bioreactor according to claim 1, wherein a space between one of the at least two cassettes and one or more of the one or more spiral-shaped tubes functions as a ventilation shaft used for cooling of the photo bioreactor, including the at least two cassettes the one or more light sources.

* * * * *